(12) United States Patent
Faden et al.

(10) Patent No.: US 9,434,945 B2
(45) Date of Patent: Sep. 6, 2016

(54) USE OF MIR-23A-3P AND/OR MIR-27A-3P MIMICS AS THERAPEUTIC AGENTS FOR INHIBITION OF NEURONAL APOPTOSIS FOLLOWING BRAIN INJURY

(71) Applicant: UNIVERSITY OF MARYLAND, BALTIMORE, Baltimore, MD (US)

(72) Inventors: Alan Faden, Baltimore, MD (US); Boris Sabirzhanov, Lutherville, MD (US); Bogdan Stoica, Bethesda, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/450,664

(22) Filed: Aug. 4, 2014

(65) Prior Publication Data
US 2015/0037403 A1   Feb. 5, 2015

Related U.S. Application Data

(60) Provisional application No. 61/861,769, filed on Aug. 2, 2013.

(51) Int. Cl.
C12N 15/11 (2006.01)
C12N 15/113 (2010.01)

(52) U.S. Cl.
CPC ....... *C12N 15/113* (2013.01); *C12N 2310/141* (2013.01)

(58) Field of Classification Search
CPC ............ C12N 15/113; C12N 2320/35; C12N 2310/141
See application file for complete search history.

(56) References Cited

U.S. PATENT DOCUMENTS

2006/0247193 A1* 11/2006 Taira .................... C12N 15/113 514/44 A

FOREIGN PATENT DOCUMENTS

WO   WO2010/033871 A2 * 3/2010

OTHER PUBLICATIONS

Madathil et al. Bioessays 2011, 33:21-26.*
Cook et al. Pharmacotherapy. Jul. 2009;29(7):832-45.*
Babar, I.A. et al. (2012) Nanoparticle-based therapy in an in vivo micro-RNA-155 (mir-155)-dependent mouse model of lymphoma, *Proc. Natl. Acad. Sci. USA*, 109, E1695-E1704.
Chen, Q. et al. (2014) MicroRNA-23a/b and microRNA-27a/b suppress Apaf-1 protein and alleviate hypoxia-induced neuronal apoptosis. *Cell death & disease*, 5:e1132.
Clark, R.S.B. et al. (2001) Detection of single- and double-strand DNA breaks after traumatic brain injury in rats: comparison of in situ labeling techniques using DNA polymerase I, the Klenow fragment of DNA polymerase I, and terminal deoxynucleotidyl transferase. *Journal of Neurotrauma* 18:675-689.
Cryns, V.L. et al. (1996) Specific cleavage of alpha-fodrin during Fas- and tumor necrosis factor-induced apoptosis is mediated by an interleukin-1beta-converting enzyme/Ced-3 protease distinct from the poly(ADP-ribose) polymerase protease. *J Biol Chem* 271:31277-31282.
Culmsee, C. et al. (2005) p53 in neuronal apoptosis. *Biochem Biophys Res Commun* 331:761-777.
Di Giovanni, S. et al. (2003) Gene profiling in spinal cord injury shows role of cell cycle in neuronal death. *Annals of Neurology* 53:454-468.
Engel, T. et al. (2011) In vivo contributions of BH3-only proteins to neuronal death following seizures, ischemia, and traumatic brain injury. *J Cereb Blood Flow Metab* 31:1196-1210.
Fox, G.B. et al. (1998) Sustained sensory/motor and cognitive deficits with neuronal apoptosis following controlled cortical impact brain injury in the mouse. *Journal of Neurotrauma* 15:599-614.
Gautier, L. et al. (2004) affy—analysis of Affymetrix GeneChip data at the probe level. *Bioinformatics* 20:307-315.
Griffiths-Jones, S. et al. (2006) miRBase: microRNA sequences, targets and gene nomenclature. *Nucleic Acids Res* 34:D140-144.
Guo, Z. et al. (2013) MiR-23a regulates DNA damage repair and apoptosis in UVB-irradiated HaCaT cells. *J Dermatol Sci* 69:68-76.
Harraz, M.M. et al. (2012) MicroRNA-223 is neuroprotective by targeting glutamate receptors. Proc Natl Acad Sci U S A 109:18962-18967.
Hu, Z. et al. (2012) Expression of miRNAs and their cooperative regulation of the pathophysiology in traumatic brain injury. PLoS One 7:e39357.
Hwang, D.W. et al. (2011) A brain-targeted rabies virus glycoprotein-disulfide linked PEI nanocarrier for delivery of neurogenic microRNA. *Biomaterials* 2011, 32, 4968-4975.
Irizarry, R.A. et al. (2003) Summaries of Affymetrix GeneChip probe level data. *Nucleic Acids Res* 31 : e15.
Jeffers, J.R. et al. (2003) Puma is an essential mediator of p53-dependent and -independent apoptotic pathways. *Cancer cell* 4:321-328.
Jimenez-Mateos, E.M. et al. (2011) miRNA Expression profile after status epilepticus and hippocampal neuroprotection by targeting miR-132. *The American journal of pathology* 179:2519-2532.
Jimenez-Mateos, E.M. et al. (2013) Epilepsy and microRNA. *Neuroscience* 238:218-229.
Kabadi, S.V. et al. (2012) CR8, a selective and potent CDK inhibitor, provides neuroprotection in experimental traumatic brain injury. Neurotherapeutics: *The journal of the American Society for Experimental NeuroTherapeutics* 9:405-421.
Kaeser, M.D. et al. (2002) Chromatin immunoprecipitation analysis fails to support the latency model for regulation of p53 DNA binding activity in vivo. *Proc Natl Acad Sci U S A* 99:95-100.

(Continued)

Primary Examiner — Brian Whiteman
(74) *Attorney, Agent, or Firm* — Marianne Fuierer; Moore & Van Allen, PLLC

(57) ABSTRACT

The present invention relates to a method for treating a brain injury due to a traumatic event, disease or ischemic attack in a mammal subject, wherein the method comprises administering to the mammal subject an effective amount of miR-23a-3p and/or miR-27a-3p mimics to reduce activation of Puma, Noxa and Bax therby causing a subsequent reduction in neuronal apoptosis.

11 Claims, 18 Drawing Sheets

(56) References Cited

OTHER PUBLICATIONS

Kole, A.J. et al. (2011) miR-29b is activated during neuronal maturation and targets BH3-only genes to restrict apoptosis. Genes Dev 25:125-130.
Le Rhun, Y. et al. (1998) Cellular responses to DNA damage in the absence of Poly(ADP-ribose) polymerase. Biochem Biophys Res Commun 245:1-10.
Lei, P. et al. (2009) Microarray based analysis of microRNA expression in rat cerebral cortex after traumatic brain injury. Brain Res 1284:191-201.
Li, P. et al. (1997) Cytochrome c and dATP-dependent formation of Apaf-1/caspase-9 complex initiates an apoptotic protease cascade. Cell 91:479-489.
Liu, X. et al. (1996) Induction of apoptotic program in cell-free extracts: requirement for dATP and cytochrome c. Cell 86:147-157.
Liu, D.Z. et al. (2010) Brain and blood microRNA expression profiling of ischemic stroke, intracerebral hemorrhage, and kainate seizures. J Cereb Blood Flow Metab 30:92-101.
Livak, K.J. et al. (2001) Analysis of relative gene expression data using real-time quantitative PCR and the 2(-Delta Delta C(T)) Method. Methods 25:402-408.
Loane, D.J. et al. (2009) Amyloid precursor protein secretases as therapeutic targets for traumatic brain injury. Nature medicine 15:377-379.
Lomonosova, E. et al. (2008) BH3-only proteins in apoptosis and beyond: an overview. Oncogene 27 Suppl 1:S2-19.
Lowe, S.W. et al. (1993) p53 is required for radiation-induced apoptosis in mouse thymocytes. Nature 362:847-849.
Nakano, K. et al. (2001) PUMA, a novel proapoptotic gene, is induced by p53. Mol Cell 7:683-694.
Oda, E. et al. (2000) Noxa, a BH3-only member of the Bcl-2 family and candidate mediator of p53-induced apoptosis. Science 288:1053-105.
Pfaffl, M.W. (2001) A new mathematical model for relative quantification in real-time RT-PCR. Nucleic Acids Res 29:e45.
Pietrzak, M. et al. (2011) Nucleolar disruption and apoptosis are distinct neuronal responses to etoposide-induced DNA damage. Journal of Neurochemistry 117:1033-1046.
Redell, J.B. et al. (2009) Traumatic brain injury alters expression of hippocampal microRNAs: potential regulators of multiple pathophysiological processes. J Neurosci Res 87:1435-1448.
Redell, J.B. et al. (2011) Altered expression of miRNA-21 and its targets in the hippocampus after traumatic brain injury. J Neurosci Res 89:212-221.
Ren, Y. et al. (2010) Co-delivery of as-miR-21 and 5-FU by poly(amidoamine) dendrimer attenuates human glioma cell growth in vitro. J. Biomater. Sci. 2010, 21, 303-314.
Rogakou, E.P. et al. (1999) Megabase chromatin domains involved in DNA double-strand breaks in vivo. J Cell Biol 146:905-916.
Sabirzhanov, B. et al. (2012) Over-expression of HSP70 attenuates caspase-dependent and caspase-independent pathways and inhibits neuronal apoptosis. Journal of Neurochemistry 123:542-554.
Selvamani, A. et al. (2012) An antagomir to microRNA Let7f promotes neuroprotection in an ischemic stroke model. PLoS One 7:e32662.
Shamas-Din, A. et al. (2011) BH3-only proteins: Orchestrators of apoptosis. Biochimica et biophysica acta 1813:508-520.
Shieh, S.Y. et al. (1997) DNA damage-induced phosphorylation of p53 alleviates inhibition by MDM2. Cell 91:325-334.
Siegel, C. et al. (2011) miR-23a regulation of X-linked inhibitor of apoptosis (XIAP) contributes to sex differences in the response to cerebral ischemia. Proc Natl Acad Sci U S A 108:11662-11667.
Siman, R. et al. (1984) Brain fodrin: substrate for calpain I, an endogenous calcium-activated protease. Proc Natl Acad Sci U S A 81:3572-3576.
Siman, R.et al. (2004) Proteins released from degenerating neurons are surrogate markers for acute brain damage. Neurobiol Dis 16:311-320.
Srinivasula, S.M. et al. (1998) Autoactivation of procaspase-9 by Apaf-1-mediated oligomerization. Mol Cell 1:949-957.
Stappert, L. et al. (2013) MicroRNA-based promotion of human neuronal differentiation and subtype specification. PLoS One 8:e59011.
Steckley, D. et al. (2007) Puma is a dominant regulator of oxidative stress induced Bax activation and neuronal apoptosis. J Neurosci 27:12989-12999.
Stoica, B.A. et al. (2003) Ceramide-induced neuronal apoptosis is associated with dephosphorylation of Akt, BAD, FKHR, GSK-3beta, and induction of the mitochondrial-dependent intrinsic caspase pathway. Mol Cell Neurosci 22:365-382.
Stoica, B.A. et al. (2005) Ceramide induces neuronal apoptosis through mitogen-activated protein kinases and causes release of multiple mitochondrial proteins. Mol Cell Neurosci 29:355-371.
Stoica, B.A. et al. (2010) Cell death mechanisms and modulation in traumatic brain injury. Neurotherapeutics: The journal of the American Society for Experimental NeuroTherapeutics 7:3-12.
Susin, S.A. et al. (1999) Molecular characterization of mitochondrial apoptosis-inducing factor. Nature 397:441-446.
Truettner, J.S. et al. (2011) Therapeutic hypothermia alters microRNA responses to traumatic brain injury in rats. J Cereb Blood Flow Metab 31:1897-1907.
Truettner, J.S. et al. (2013) MicroRNA overexpression increases cortical neuronal vulnerability to injury. Brain Res 1533:122-130.
Vousden, K.H. (2005) Apoptosis. p53 and PUMA: a deadly duo. Science 309:1685-1686.
Yakovlev, A.G. et al. (2001) Differential expression of apoptotic protease-activating factor-1 and caspase-3 genes and susceptibility to apoptosis during brain development and after traumatic brain injury. J Neurosci 21:7439-7446.
Yakovlev, A.G. et al. (2004) BOK and NOXA are essential mediators of p53-dependent apoptosis. J Biol Chem 279:28367-28374.
Yan, H. et al. (2013) Isoflurane increases neuronal cell death vulnerability by downregulating miR-214. PLoS One 8:e55276.
Yang, X. et al. (2012) Differentially expressed plasma microRNAs in premature ovarian failure patients and the potential regulatory function of mir-23 a in granulosa cell apoptosis. Reproduction 144:235-244.
Ziu, M. et al. (2011) Temporal differences in microRNA expression patterns in astrocytes and neurons after ischemic injury. PLoS One 6:e14724.

* cited by examiner

SEQUENCE LISTING

```
<160> NUMBER OF SEQ ID NOS: 8

<210> SEQ ID NO 1
<211> LENGTH: 21
<212> TYPE: RNA
<213> ORGANISM: Artificial Sequence
<220> FEATURE:
```

<223> OTHER INFORMATION: Synthetic Construct

<400> SEQUENCE: 1
aucacauugc cagggauuuc c                                           21

<210> SEQ ID NO 2
<211> LENGTH: 21
<212> TYPE: RNA
<213> ORGANISM: Artificial Sequence
<220> FEATURE:
<223> OTHER INFORMATION: Synthetic Construct

<400> SEQUENCE: 2
uucacagugg cuaaguuccg c                                           21

<210> SEQ ID NO 3
<211> LENGTH: 26
<212> TYPE: DNA
<213> ORGANISM: Artificial Sequence
<220> FEATURE:
<223> OTHER INFORMATION: Synthetic Construct

<400> SEQUENCE: 3
tgtctagagt gcctacaccc gcccgg                                      26

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
tggtcgacca ctgttcaatc tgattttatt gaaaagga                         38

<210> SEQ ID NO 5
<211> LENGTH: 28
<212> TYPE: DNA
<213> ORGANISM: Artificial Sequence
<220> FEATURE:
<223> OTHER INFORMATION: Synthetic Construct

<400> SEQUENCE: 5
tgtctagagt tcttccaaag cttttgca                                    28

<210> SEQ ID NO 6
<211> LENGTH: 38
<212> TYPE: DNA
<213> ORGANISM: Artificial Sequence
<220> FEATURE:
<223> OTHER INFORMATION: Synthetic Construct

<400> SEQUENCE: 6
tggtcgacgc atttttcaat agttacttta gtatcaac                         38

<210> SEQ ID NO 7
<211> LENGTH: 26
<212> TYPE: DNA
<213> ORGANISM: Artificial Sequence
<220> FEATURE:
<223> OTHER INFORMATION: Synthetic Construct

<400> SEQUENCE: 7
tgtctagagg cctcccactg ccttgg                                      26

```
<210> SEQ ID NO 8
<211> LENGTH: 31
<212> TYPE: DNA
<213> ORGANISM: Artificial Sequence
<220> FEATURE:
<223> OTHER INFORMATION: Synthetic Construct

<400> SEQUENCE: 8
tggtcgacta caatccaaag tggacctgag g                              31
```

USE OF MIR-23A-3P AND/OR MIR-27A-3P MIMICS AS THERAPEUTIC AGENTS FOR INHIBITION OF NEURONAL APOPTOSIS FOLLOWING BRAIN INJURY

CROSS-REFERENCE TO RELATED APPLICATION

The present application claims priority to co-pending U.S. Provisional Application No. 61/861,769, filed on Aug. 2, 2013, the contents of which is hereby incorporated by reference herein for all purposes.

STATEMENT OF GOVERNMENT RIGHTS

This invention was made with government support under Grant Number NS061839 awarded by the National Institutes of Health. The government has certain rights in the invention.

BACKGROUND OF THE INVENTION

1. Field of the Invention

The present invention relates to reduction of apoptosis in brain tissue and cells, and more particularly, to the use of miR-23a-3p and/or miR-27a-3p mimics as therapeutic agents to reduce neuronal apoptosis in injured brain tissue and cells.

2. Description of the Related Art

Traumatic brain injury (TBI) occurs when an outside force impacts the brain and such injury is usually due to a brief event occurring in less than a second. Such an injury may be due to a vehicular accident, a violent act or a sports-related injury. The main problem associated with TBI is neuronal cell death and the outcome of TBI ranges from complete recovery to permanent disability, and sometimes death. Also, TBI initiates secondary cell death mechanisms that contribute to tissue damage and neurological dysfunction (Stoica and Faden, 2010).

Neuronal cell death is also found in many other human neurological disorders including Alzheimer's, Parkinson's and Huntington's disease, stroke and amyotrophic lateral sclerosis (ALS). Neurons in the brain are interconnected and if the functional connections are separated the result is impaired brain function. Clearly, understanding how to regulate apoptosis could be the first step to treating these brain injuries or diseases.

Brain trauma due to any of the other above described diseases or injuries is usually associated with regional apoptosis. Apoptotic cell death is a highly regulated cellular process in which a cell is instructed to shut itself down and is eliminated. Apoptosis initiates a cascade of intracellular events to effect cell death and particularly suppresses the expression of expression of anti-apoptotic factor B-cell lymphoma-2 (Bcl-2) proteins.

The Bcl-2 family of proteins includes both pro- and anti-apoptotic members. Full members of the Bcl-2 family share homology in four conserved domains designated BH1, BH2, BH3 and BH4. BH3 includes proteins, such as, Puma, Noxa, Bid and Bim all of which promote neuronal cell death by binding and inactivating anti-apoptotic Bcl-2 family members, and by direct activation of pro-apoptotic multi-BH domain proteins (Bax and Bak), which ultimately cause release of pro-apoptotic molecules from mitochondria (cytochrome c and apoptosis inducing factor (AIF)) (Lomonosova and Chinnadurai, 2008; Shamas-Din et al., 2011). BH3-only proteins have been implicated in neuronal cell death after CNS injury, including TBI (Engel et al., 2011). The mechanisms responsible for up-regulation and activation of BH3-only proteins include both p53 dependent and independent mechanisms (Jeffers et al., 2003; Yakovlev et al., 2004).

MicroRNAs (miRs) are a broad class of small non-coding RNAs that control diverse biological processes including major signaling pathways by regulating the expression of complementary target mRNAs. miRs are short (20-23 nucleotide) noncoding RNAs that negatively regulate gene expression at the post-transcriptional level by binding to the 3'-untranslated region (UTR) of target mRNAs, leading to their degradation and/or translational inhibition (Griffiths-Jones et al., 2006). Recent studies indicate that miRs are involved in the pathophysiology of brain seizures, ischemia and trauma (Lei et al., 2009; Redell et al., 2009 ; Liu et al., 2010; Ziu et al., 2011). miRs modulate neuronal cell death pathways (Jimenez-Mateos and Henshall, 2013), but few have been directly evaluated in the context of TBI or other brain injury (Siegel et al., 2011; Selvamani et al., 2012), and thus, their mechanisms of action in this regard remains largely unknown.

miR-23a may play an important role in regulation of apoptosis in human ovarian granulosa cells (Yang et al., 2012) and human keratinocytes (Guo et al., 2013), as well as in sex-dependent regulation of X-linked inhibitor of apoptosis (XIAP) following cerebral ischemia (Siegel et al., 2011). Previous studies that examined miR modulation after TBI have been largely descriptive, and have focused only tangentially on the miR-23a~27a~24-2 cluster and encoding primary miRNAs transcript (pri-miRNA) (Lei et al., 2009; Truettner et al., 2011; Hu et al., 2012).

As such, it would be advantageous to identify new agents and mechanisms that can reduce neuronal apoptosis thereby providing new approaches for treating neurodegenerative disorders or TBI.

SUMMARY OF THE INVENTION

The present invention relates to the finding that miR-23a and-27a are rapidly down-regulated in the injured cortex in the first hour after TBI. These changes coincided with increased expression of the pro-apoptotic Bcl-2 family members Noxa, Puma, and Bax. Importantly, it has been found by the present inventors that administration of miR-23a-3p and/or miR-27a-3p mimics significantly reduced activation of Puma, Noxa and Bax as well as attenuated markers of caspase-dependent and -independent apoptosis following TBI. Furthermore, miR-23a and miR-27a mimics significantly attenuate cortical lesion volume and neuronal cell loss in the hippocampus following TBI. These findings indicate that posttraumatic decreases in miR-23a and -27a contribute to neuronal cell death after TBI by up-regulating pro-apoptotic Bcl-2 family members. The methods described herein involve the direct and/or indirect reduction of apoptosis in neuronal cells in a treated subject by administering miR-23a and/or miR-27a mimics, which heretofore were unknown as therapeutic agents.

One aspect of the present invention provides for a method of treating a brain injury due to a traumatic event, disease, or ischemic attack in a mammal subject in need of treatment thereof, the method comprising administering to the mammal subject an effective amount of a miR-23a-3p and/or miR-27a-3p mimic to reduce activation of Puma, Noxa and Bax as well as attenuated markers of caspase-dependent and -independent apoptosis following TBI.

The miR-23a-3p and miR-27a-3p mimics are double stranded nucleic acid molecules and comprise the sequences of AUCACAUUGCCAGGGAUUUCC (SEQ ID NO: 1) and UUCACAGUGGCUAAGUUCCGC (SEQ ID NO: 2), respectively.

A traumatic event may include an inertia injury due to sudden acceleration or deceleration, impact injury, such as, being hit with a lacrosse ball or baseball bat, or a penetrating injury, such as, a gun shot. Diseases may include Alzheimer's, Parkinson's and Huntington's disease and amyotrophic lateral sclerosis (ALS). Further, traumatic injury to the spinal cord can cause damage distal to the point of injury, and thus, is considered to be a targeted disorder. Notably, a traumatic injury to the brain area is usually a two-step process, the primary injury which is the initial damage to the neurons and preferred treatment is initiated within a few hours of the injury or more preferably with one hour to ten hours of the injury. Secondary injury which is a progressive response over days, weeks and months provides a window of time in which the miR-23a-3p and/or miR-27a-3p mimics of the present invention can be administered.

In another aspect, the present invention provides a method of protecting neuron cells from cell death in a subject, the method comprising the step of supplying to the cell an effective amount of a composition comprising a miR-23a-3p mimic and/or miR-27a-3p mimic. In one specific embodiment, the mimic comprises a nucleotide sequence selected from the group consisting of AUCACAUUGCCAGGGAUUUCC (SEQ ID NO: 1) and UUCACAGUGGCUAAGUUCCGC (SEQ ID NO: 2).

In yet another aspect, the present invention provides for a pharmaceutical composition comprising one or more miRNAs selected from the group consisting of miR-23a-3p mimic and miR-27a-3p mimic. The composition may further comprise a pharmaceutically acceptable excipient. Preferably, the amount of the miR-23a-3p mimic and/or miR-27a-3p mimic is from about 1 nanomole to about 1 micromole per kg of body weight, and more preferably, from about 10 nanomoles to about 100 nanomoles per kg of body weight, e.g., from about 10 nanomoles to about 50 nanomoles per kg of body weight; from about 10 nanomoles to about 40 nanomoles per kg of body weight; from about 10 nanomoles to about 30 nanomoles per kg of body weight; from about 20 nanomoles to about 50 nanomoles per kg of body weight; from about 20 nanomoles to about 60 nanomoles per kg of body weight; from about 20 nanomoles to about 80 nanomoles per kg of body weight; e.g., about 10, about 20, about 30, about 40, about 50, about 60, about 70, about 80, about 90, about 100 nanomoles per kg of body weight.

In another aspect, the present invention provides for a recombinant vector comprising the nucleotide sequences for the miR-23a-3p mimic and/or the miR-27a-3p mimic.

In a further aspect, the present invention provides a method for blocking a step in the apoptotic biochemical cascade to reduce neuronal death, the method comprising:

contacting neuronal tissue or cells with a miRNA mimic in an amount sufficient to target pro-apoptotic genes downstream of p53 including PUMA, Noxa and/or Bax and cause down-regulation of PUMA, Noxa and/or Bax. Preferably the neural cells are transfected with a miR-23a-3p and/or a miR-27a-3p mimic.

Other aspects, features and embodiments of the invention will be more fully apparent from the ensuing disclosure and appended claims.

DETAILED DESCRIPTION OF THE INVENTION

Figure 1:
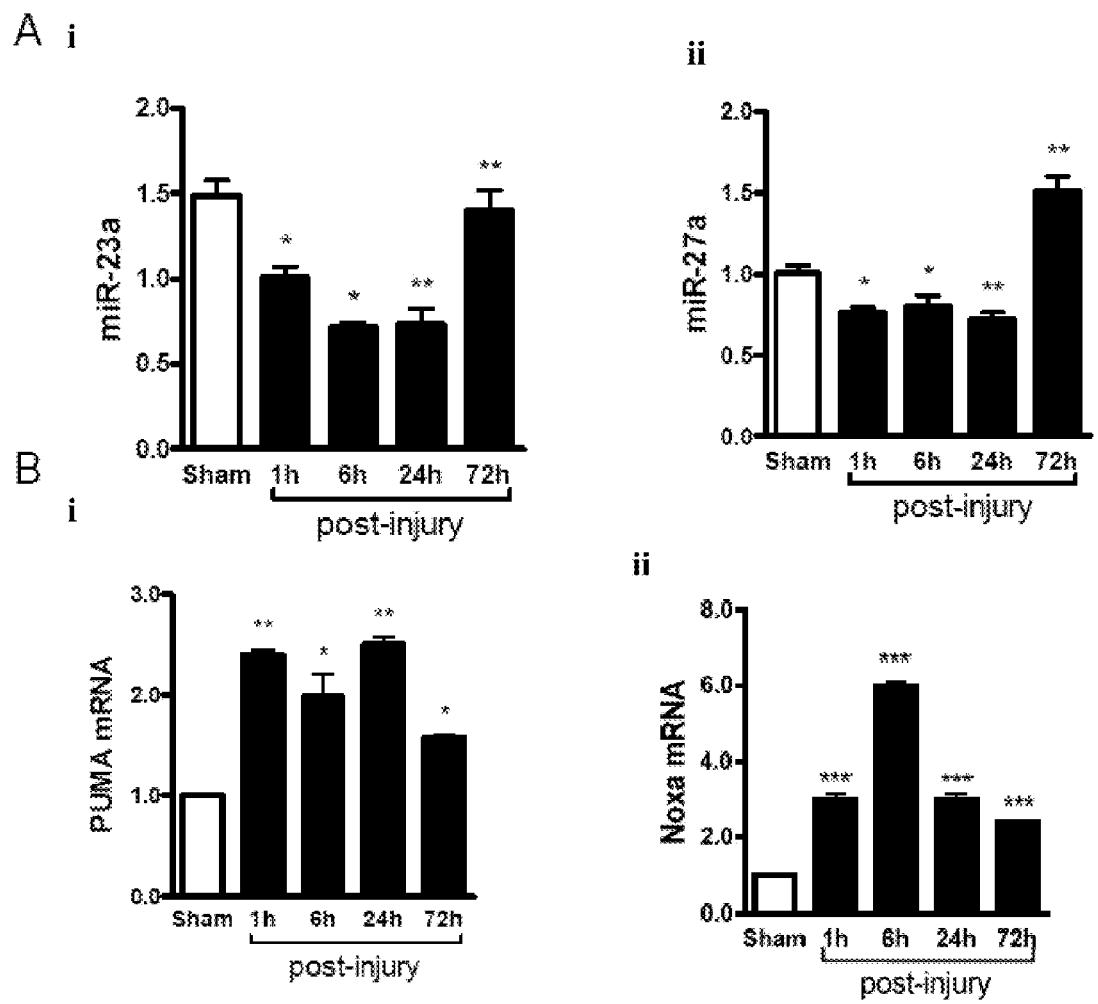
FIG. 1 shows miR-24-3p and miR-27a-3p down-regulation in the mouse injured cortex after TBI is associated with increased mRNA levels for Bcl-2 family pro-apoptotic molecules. (A) Analysis of qPCR data for miR-23a-3p (i) and -27a-3p (ii) expression at different time points after TBI in mouse cortex after TBI, normalized to snoRNA202. Data represent the mean±S.D. *-P<0.05; -P<0.01; *-P<0.001 vs. control animals (N=5). (B) qPCR quantification of expression of pro-apoptotic genes Noxa (ii) and Puma (i) in mouse cortex at different time points after TBI, normalized to GAPDH. Data represent the mean±S.D. *-P<0.05; -P<0.01; *-P<0.001 vs. sham animals (N=5). Analysis by one-way ANOVA followed by multiple pairwise comparisons using Student-Newman-Keuls post-hoc test. Non-parametric Kruskal—Wallis one-way ANOVA followed by multiple pairwise comparisons using Dunn's post hoc test was used for analysis of Bim expression.

Temporal profiling of miR changes were performed following controlled cortical impact and focused on the first hours and days after trauma, a period associated with maximal secondary neuronal cell death (Stoica and Faden, 2010). It was found that miRs undergo a rapid decline during this period and it was also found to negatively regulate pro-apoptotic molecules leading to TBI-induced activation of neuronal cell death pathways. DNA damage including DNA breaks produced by oxidative injury and other mechanisms is a key inducer of neuronal cell death after TBI (Clark et al., 2001). Etoposide is an anti-cancer drug that produces DNA breaks in neurons by inhibiting DNA-topoisomerase-II resulting in caspase-dependent and -independent apoptosis (Pietrzak et al., 2011); (Sabirzhanov et al., 2012). miR changes and their effects on cell death pathways were examined following etoposide-induced DNA damage in primary neurons. miR-23a and -27a were investigated because 1) they were down-regulated in the acute time period associated with intense neuronal cell death; 2) these two miRs are the members of the same genomic cluster, expressed together as single primary transcript and found to target members of the pro-apoptotic Bcl2 family.

Definitions

Unless otherwise defined, all technical and scientific terms used herein have the same meaning as commonly understood by one of ordinary skill in the art to which this invention belongs. In case of conflict, the present application, including definitions, will control.

As used herein, the term "miRNA mimic" refers to an oligonucleotide which comprises a double stranded nucleic acid molecule, wherein the nucleic acid molecule has a similar or identical activity with a miRNA molecule and is capable of binding to a target gene (either the mRNA or the DNA) and regulating expression of that gene.

As used herein the term "effective amount of the miRNA mimic" refers to an amount sufficient to be effective in treating or preventing a disorder or to regulate a physiological condition in a mammals and specifically humans.

As used herein the terms "treatment" or "treating" refer to the administration of a therapeutic agent (e.g., a miRNA mimic or vector or transgene encoding same) to a patient, or application or administration of a therapeutic agent to an isolated tissue or cell line from a patient who has the disease or disorder or a symptom of disease or disorder with the purpose to heal, alleviate, relieve, improve or affect the disease or disorder or the symptoms of the disease or disorder.

In certain embodiments, the miRNA mimic may be linked (covalently or non-covalently) to one or more moieties or conjugates that enhance the activity, cellular distribution, or cellular uptake of the oligonucleotide. Such moieties include, without limitation, lipid moieties such as cholesterol, cholic acid, a thioether, an aliphatic chain, a phospholipid, a polyamine or a polyethylene glycol chain.

In certain embodiments, the miRNA mimics of the present invention are expressed from a recombinant vector. Suitable recombinant vectors include, without limitation, DNA plasmids, viral vectors or DNA minicircles. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989

In certain embodiments, miRNA mimics agents used to practice this invention are synthesized in vitro using chemical synthesis techniques known to skilled artisans.

The present invention provides for a method of treating brain injuries or diseases. Such methods of treatment may be specifically tailored for an individual's prophylactic or therapeutic treatment with miRNAs mimics of the present invention. The miRNA mimics of the present invention can also be tested in an appropriate animal model to determine the efficacy, toxicity, or side effects of treatment with said miRNA mimics.

Certain factors may influence the dosage required to effectively treat a subject, including but not limited to the severity of the brain injury or brain disease, previous treatments, the general health and/or age of the subject, and other diseases present. Moreover, treatment of a subject with a therapeutically effective amount of a miRNA mimic can include a single treatment or can include a series of treatments. It will also be appreciated that the effective dosage of a miRNA mimic for treatment may increase or decrease over the course of a particular treatment. Changes in dosage may result and become apparent from the results of diagnostic assays as described herein.

Delivery of a miRNA mimic of the present invention can be administered by injection (e.g., intravenous, intramuscular or intracerebroventricular), an inhaled dose, or a topical application and in an amount from about 1 nanomole to about 10 micromoles per kg of body weight and more preferably from about 10 nanomoles to about 100 nanomoles per kg of body weight (e.g., from about 10 nanomoles to about 50 nanomoles per kg of body weight; from about 10 nanomoles to about 40 nanomoles per kg of body weight; from about 10 nanomoles to about 30 nanomoles per kg of body weight; from about 20 nanomoles to about 50 nanomoles per kg of body weight; from about 20 nanomoles to about 60 nanomoles per kg of body weight; from about 20 nanomoles to about 80 nanomoles per kg of body weight; e.g., about 10, about 20, about 30, about 40, about 50, about 60, about 70, about 80, about 90, about 100 nanomoles per kg of body weight).

In one embodiment, the unit dose is administered daily or less frequently than once a day, e.g., less than every 2, 4, 8 or 30 days. In a further embodiment, the unit dose may be administered a single time. In another embodiment, the effective dose is administered with other traditional therapeutic modalities.

In a certain embodiment, a subject is administered an initial dose, and one or more maintenance doses of a miRNA mimic. The maintenance doses are preferably administered no more than once every 5, 10, or 30 days. Further, the treatment regimen may last for a period of time which will vary depending upon the nature of the particular brain disease, its severity and the overall condition of the patient.

Viral and non-viral delivery have been used for delivery methods. A variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. Adenovirus-associated vectors (AAV) are an appealing method since they have acceptable toxicity profiles and have been successfully used to restore miRNA expression. Different AAV serotypes can successfully target different neuronal tissue.

miRNA mimics may be directly introduced into a cell or into the circulation of an organism. Vascular or extravascular circulation, the blood or lymph system, and the cerebrospinal fluid are sites where the miRNA mimics may be introduced.

Non-viral delivery can be used as an efficient system to deliver the miRNA mimics. For example, liposomes composed of phospholipid bilayers can be used, however, such use is limited by their toxicity due to their strong cationic charge. Hyaluronic acid can be used to improve their stability and minimize the side effects. To overcome the toxicity of liposomes, a neutral lipid emulsion can be used, such as the inclusion of polyethylenimines (PEIs). These positively charged polymers bind to miRNA mimics to form nanoscale complexes leading to cellular delivery. Importantly the complex retains an overall positive charge that interacts with negatively charged polysaccharides on the cell surface allowing for the release of the compound containing the miRNA in the cytoplasm. Notably this PEI system can be used to cross the blood brain barrier by using a rabies virus glycoprotein or mannitol to deliver a neuron specific miRNA mimic to the brain cells. (Hwang, et al., 2011)

Other forms of non-viral delivery systems include dendrimers which are repetitively-branched perfectly-structured particles that have a high surface to volume ratio and can be used to deliver miRNA mimics to neuronal cells. (Ren, Y., et al. 2010). Further delivery can be accomplished by the use of polylactide-co-glycolide (PLGA) particles which are stable particles that allow the delivery of miRNA over time and are highly adaptable and can be used to load multiple cargos. PLGA particles delivered anti-miRNA-155 to malignant pre-B lymphoma cells in mouse models with good results. (Babar, I.A.; et al. 2012).

In a certain embodiment, the methods disclosed herein can include the administration of pharmaceutical formulations comprising miRNA mimics capable of reducing the expression of PUMA, Noxa and/or Bax and thereby causing a reduction in neuronal apoptosis. These formulations can comprise pharmaceutically acceptable carriers and other vehicles and solvents. For example, water, Ringer's solution and isotonic sodium chloride may be used. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The present invention is further illustrated by the following examples which should not be construed as further limiting.

EXAMPLES

Materials and Methods

Animals—Studies were performed using young adult (3-month-old, 22-26 g) male C57B1/6 mice which were housed under a 12-hour light-dark cycle, with ad libitum access to food and water. All surgical procedures complied with the Guide for the Care and Use of Laboratory Animals published by NIH (DHEW publication NIH 85-23-2985), and the protocols were approved by the University of Maryland School of Medicine Institutional Animal Care and Use Committee (IACUC).

Controlled cortical impact injury—The custom-designed Controlled Cortical Impact (CCI) injury device (Fox et al., 1998) consists of a microprocessor-controlled pneumatic impactor with a 3.5 mm diameter tip. Young adult male C57B1/6 mice were anesthetized with isoflurane evaporated in a gas mixture containing 70% $N_2O$ and 30% $O_2$ and administered through a nose mask (induction at 4% and maintenance at 2%). Depth of anesthesia was assessed by monitoring respiration rate and pedal withdrawal reflexes. Mice were placed on a heated pad, and core body temperature was maintained at 37° C. The head was mounted in a stereotaxic frame, and the surgical site was clipped and cleaned with Nolvasan and ethanol scrubs. A 10-mm midline incision was made over the skull, the skin and fascia were reflected, and a 4-mm craniotomy was made on the central aspect of the left parietal bone. The impounder tip of the injury device was then extended to its full stroke distance (44 mm), positioned to the surface of the exposed dura, and reset to impact the cortical surface. Moderate-level injury was induced using an impactor velocity of 6 m/s and deformation depth of 2 mm as previously described (Loane et al., 2009). After injury, the incision was closed with interrupted 6-0 silk sutures, anesthesia was terminated, and the animal was placed into a heated cage to maintain normal core temperature for 45 minutes post-injury. All animals were monitored for at least 4 hours after surgery and then daily. Sham-injured animals underwent anesthesia and surgical procedures but without cortical impact.

icy injections—At 15 minutes post-injury, mice received a single intracerebroventricular (icy) injection of miR-23a-3p, miR-27a-3p or negative control miR mimics. All drugs were made up in a Cerebrospinal fluid (CSF), and drugs were injected into the left ventricle (coordinates from bregma=A: −0.5, L: −1.0, V: −2.0) using a 30 gauge needle attached to a Hamilton syringe at a rate of 0.5 ml/min, with a final volume of 5 μl of 0.1 mM miR mimic solution.

Cell cultures—Rat cortical neurons (RCN) were derived from rat embryonic cortices. Cells were seeded onto poly-d-lysine-coated 96-well or 24-well plates or 100-mm Petri dishes (cell density $1\times10^6/cm^2$) and maintained in serum-free conditions using the B27 supplement as described (Yakovlev et al., 2001). Transfection of RCN was performed at 6 days in vitro (DIV). RCN were transfected with miR mimics and hairpin inhibitors using the Lipofectamine® RNAiMAX Transfection Reagent. Lipofectamine® 2000 (Invitrogen, Life Technologies) was used for RCN co-transfection with plasmid and miR mimics according to the manufacturer's protocol. The concentrations of miRs mimics and hairpin inhibitors commonly used for transfection are in the range 10-100 nM (Stappert et al., 2013; Yan et al., 2013). Based on preliminary titration experiments a final concentration of 50 nM was chosen for the miR mimics and hairpin inhibitors. This concentration resulted in optimal transfection efficiency, was devoid of non-specific changes in non-targeted miRs and had no unwanted neurotoxic effects. Moreover, the chosen concentration was associated with peak neuroprotective effects (data not shown). Four hours after transfection, media was replaced with normal condition media and cells treated with etoposide at a final concentration 50 μM. The following miR mimics and hairpin inhibitors were used: miRIDIAN microRNA Mimic Negative Control (-ye con mimic) (CN-001000-01-05); miRIDIAN Mimic, Rat mo-miR-23a-3p (C-320309-03-0005); miRIDIAN Mimic, Rat rno-miR-27a-3p (C-320317-03-0005); miRIDIAN microRNA Hairpin Inhibitor Negative Control (-ye con inhibit) (IN-001005-01-05); miRIDIAN microRNA Rat rno-miR-23a-3p Hairpin Inhibitor (IH-320309-05-0005); miRIDIAN microRNA Rat mo-miR-27a-3p Hairpin Inhibitor (IH-320317-05-0005) (Thermo Scientific). Sequences of both miRIDIAN microRNA Mimic Negative Control and miRIDIAN microRNA Hairpin Inhibitor Negative Control are based on C. elegans microRNAs and have minimal sequence identity in human, mouse, and rat.

The human neuroblastoma SH-SY5Y cells were seeded in 96-well plates and maintained in Dulbecco's modified Eagle's medium (Life Technologies, Grand Island, N.Y., USA) supplemented with 10% fetal calf serum, 100 U/mL penicillin, and 100 U/mL streptomycin in a humid atmosphere of 5% CO2 and 95% air at 37° C. Cells at 70% confluence were transfected with plasmids. Transfection of cells was performed by using Lipofectamine 2000 Reagent (Invitrogen, Carlsbad, Calif., USA) according to manufacturer's protocol.

Cell death, cell viability and in plate fluorometric caspase-3 assays—Cell death, cell viability and in-plate fluorometric caspase-3 activity were measured as previously described using the LDH, Calcein AM and DEVD-AMC assays, respectively (Stoica et al., 2003) on Biotek Synergy Ht Microplate Reader (BioTek). Each individual treatment/time point reflects six replicates for all assays performed on cortical neurons cultured in 96-well plates; all wells were plated with and contained the same number of cells.

Construction of reporter plasmids and Luciferase assays—Oligonucleotide pairs were annealed, ligated, and cloned into pmirGLO vector (Promega) digested with XbaI and SalI according to manufacturer protocol. Oligonucleotides contained an exact match to the 2lbp mmu-miR-23a-3p and -27a-3p target sequence were used to produce pmiR-23aGlo and pmiR-27aGlo plasmids. Internal restriction sites for NotI were added in flanking sequences of oligonucleotides for clone confirmation. To produce reporter plasmids containing 3' UTRs of mouse PUMA, Noxa and Bax, sequences were PCR-amplified, digested, gel purified, ligated and cloned into pmirGLO vector (Promega) digested with XbaI and SalI restriction enzymes. The following primers were used to amplify 3'UTR of mouse PUMA, Noxa and Bax: PUMA 3'UTR forward primer 5'-tgTCTAGAGT-GCCTACACCCGCCCGG-3'(SEQ ID NO: 3), reverse primer 5'-tgGTCGACCACTGTTCAATCTGATTTTATT- GAAAAGGA-3' (SEQ ID NO: 4); Noxa 3'UTR forward primer 5'-tg TCTAGAGTTCTTCCAAAGCTTTTGCA -3' (SEQ ID NO:5), reverse primer 5'-tgGTCGACG-CATTTTTCAATAGTTACTTTAGT ATCAAC-3'(SEQ ID NO: 6); Bax 3'UTR forward primer 5'-tgTCTAGAGGC-CTCCCACTGCCTTGG-3' (SEQ ID NO: 7), reverse primer 5'-tgGTCGACTACAATCCAAAGTGGACCTGAGG-3' (SEQ ID NO: 8). XbaI site was added on 5' end of forward primers and SalI site was added to 5' end of reverse primers for cloning into pmirGLO vector XbaI, SalI digested vector (XbaI and SalI sites are marked bold). RCN or SH-SY5Y were cultured in 96-well plates and transfected as described above. All assays were performed at 24 h after transfection with the dual luciferase assay (Promega) on Biotek Synergy Ht Microplate Reader (BioTek). Firefly luciferase activity was normalized to Renilla luciferase activity. Experiments were performed in triplicate.

RNA isolation—Total RNA was isolated using miRNeasy Kit (Qiagen). During the process of isolation, samples were treated with RNase-free DNase (Qiagen) to digest DNA contamination of the samples according to the manufacturer's protocol.

miRNA arrays and miRNA array data analysis—100 ng of total RNA was used for miRs expression profiling using Affymetrix GeneChip miRNA 2.0 Arrays (Affymetrix). Briefly, total RNA from cells was extracted as described above. RNA quality and quantity was assessed via spectrophotometer (Nanodrop 1000; Thermo Scientific, Waltham, Mass.) and also via analysis of RNA Integrity Number (RIN) using the Agilent Bioanalyzer (Agilent Technologies, Santa Clara, Calif.). Double stranded cDNA was prepared from RNA and used as the template for in vitro transcription to prepare biotinylated cRNA. The target was fragmented and hybridized to probes using standard Affymetrix protocols. Affymetrix's miRNA QC Tool was used to evaluate quality control on all image data. Expression values were computed using normalization function RNA (Irizarry et al., 2003) from Bioconductor's affy (Gautier et al., 2004) package. Only values annotated as mouse probes (Mmu) were further considered. Expression values for the dataset were fitted to a linear model in order to determine differentially expressed miRNAs between different time points. Bioconductor's package LIMMA (Gentleman, 2005) was used for this task. Comparisons were made between the control group (time 0 h) and each of the injured groups (times 1 h, 6 h, 24 h and 72 h; n=3 arrays per group/time). Those miRNAs showing an adjusted p-value (False Discovery Rate [FDR] lower than 0.05 for any of these comparisons, were determined to be differentially expressed and selected for further analysis.

qPCR—VersoTM cDNA Kit (Thermo Scientific) was used to synthesize cDNA from purified total RNA. RNA (1 µg) was heated to 70° C. for 5 min and mixed with 5×cDNA-synthesis buffer, dNTP mix (0.5 nM final concentration) and Verso Enzyme Mix, and finally random hexamers (400 ng/µL) were added. Tubes were incubated at 42° C. for 30 min, followed by 95° C. for 2 min. Quantitative real-time PCR amplification was performed by using cDNA TaqMan® Universal Master Mix II (Applied Biosystems). In brief, reactions were performed in duplicate containing 2×TaqMan® Universal Master Mix II, 1 µL, of cDNA (corresponding to 50 ng RNA/reaction) and TaqMan®0 Gene Expression Assay (Applied Biosystems), 20×in a final volume of 20 µL. TaqMan® Gene Expression assays for following mouse genes were performed: GAPDH (Mm99999915_g1), Noxa (Mm00451763_m1), PUMA (Mm00519268_m1), Bim (Mm00437796_m1), Bak1 (Mm00432045_m1), Xiap (Mm00776505_m1), Map4k4 (Mm00500812_m1), Map2k7 (Mm00488765_g1); Calpain-6, (Mm00500361_m1), Calpain-7 (Mm00486697_m1); for rat: GAPDH (Rn01775763_g1), Noxa (Rn01494552_m1), Puma (Rn00597992_m1), Bim (Rn00674175_m1), Bak1 (Rn01429084_m1), Xiap (Rn01457299_m1), Bax (Rn02532082_g1), Map4k4 (Rn01437980_m1), Map2k7 (Rn01403106_m1), Calpain-6 (Rn00582574_m1), Calpain-7 (Rn01453530_m1) (Applied Biosystems). Reactions were amplified and quantified using a 7900HT Fast Real-Time PCR System and the corresponding software (Applied Biosystems). The PCR profile consisted of one cycle at 50° C. for 2 min and 95° C. for 10 min, followed by 40 cycles at 95° C. for 15 s and 60° C. for 1 min. All reactions were performed twice. Efficiency of reactions for each set gene expression was close to 100%. Efficiency of reactions was measured using the CT slope method. Briefly, serial dilutions of samples were generated and real-time RT-PCR reactions were performed on each dilution. The CT values were then plotted versus the log of the dilution and a linear regression was performed. Efficiency=(10-1/slope-1)×100% (Pfaffl, 2001). Samples were confirmed to be free of DNA contamination by performing reactions without reverse transcriptase. Gene expression was normalized to GAPDH, and the relative quantity of mRNAs was calculated based on the comparative Ct method (Livak and Schmittgen, 2001).

miR Reverse Transcription—Quantitative real-time PCR was used to measure expression of individual miR-23a and 27-a. 10 ng of total RNA was reverse transcribed using TaqMan miRNA Reverse Transcription Kit (Applied Biosystems Inc.) with miRNA-specific primers. Reverse Transcription reaction products (1.5 ul) were used for qPCR as described above. TaqMan® Gene Expression assays for following miRs were used: miR-23a (000399); miR-27a (000408); miR-24 (000402); miR-23b (000400); miR-27b (000409); U6 snRNA (001973) snoRNA202 (001232) (Applied Biosystems).

Antibodies—Antibodies from different vendors were used in this study. Abcam: V5 (ab27674), Histone H2A.X (ab11175); Santa Cruz Biotechnology: AIF (sc-13116), Apaf-1 (sc-65890), cytochrome c (sc-13560), FAS (sc-716), Bim (sc-11425); Cell Signaling Technology, Inc.: Cleaved Caspase-3 (#9661), Cleaved PARP (#9545); Phospho-Histone H2A.X (Ser139) (#9718) Phospho-p53 (SerlS) (#9284), p53 (1C12) (#2524), Bax (#2772), XIAP (#2042); Enzo Life Sciences, Inc.: GAPDH (ADI-CSA-335), Bax (active monomer) (ALX-804-224-C100), α-Fodrin, (BML-FG6090); ProSci Incorporated: PUMA (#3041), Noxa (#2437); EMD Millipore Corporation: Bak (06-536); Sigma: β-actin (A1978).

Cell lysates preparation and western blot—Whole-cell extracts were prepared as described previously (Stoica et al., 2005). A portion of the lysate (20 µg of protein) was then fractionated by sodium dodecyl sulfate-polyacrylamide gel electrophoresis (SDS-PAGE). Western blot was performed as described previously (Stoica et al., 2005). Membranes were washed and protein complexes were visualized using SuperSignal West Dura Extended Duration Substrate (Pierce). Chemiluminescence was captured on a Kodak Image Station 4000R station (Carestream Health), and protein bands were quantified by densitometric analysis using Carestream Molecular Imaging Software. The images were acquired under conditions that did not cause saturation of the signal. The data presented reflect the intensity of the target protein band compared to the control and were normalized based on the intensity of the endogenous control for each sample (expressed in arbitrary units).

Subcellular fractionation—Subcellular fractionation was performed as described (Stoica et al., 2005) with some modifications. RCN were harvested and washed in ice-cold phosphate-buffered saline (PBS). Cell suspension was centrifuged at 500 g for 15 min at 4° C. Cell pellet was resuspended for 10 min on ice in the digitonin lysis buffer (20 mM HEPES, pH 7.4, 80 mM KCl, 1 mM EDTA, 1 mM EGTA, 1 mM DTT, 250 mM Sucrose, 200 µg/mL Digitonin and Protease Inhibitor and Phosphatase Inhibitor (2, 3) cocktails (P8340; P5726 Sigma-Aldrich). The lysate was centrifuged at 1000 g for 5 min at 4° C. to pellet the nuclei. The supernatant was transferred to a new tube and centrifuged again at 12 000 g for 10 min at 4° C. to pellet the mitochondria. The resulting supernatant, representing the cytosolic fraction, was recovered. Nuclear and mitochondrial lysates were prepared in RIPA buffer (Teknova) with Protease Inhibitor Cocktail (P8340 Sigma-Aldrich).

Lesion volume assessment—Mice were euthanized and transcardially perfused with saline and 10% buffered formalin phosphate solution (containing 4% paraformaldehyde; Fisher Scientific, Pittsburg, Pa.) on post-injury day 28. Lesion volume was determined based on the Cavalieri method as previously described (Kabadi et al., 2012) using Stereoinvestigator software (MBF Biosciences, Williston, Vt.).

Assessment of neuronal cell loss in hippocampal sub-regions—Stereoinvestigator software (MBF Biosciences) was used to count the total number of surviving neurons in the Cornu Ammonis (CA) 1, CA2/3, and dentate gyrus (DG) sub-regions of the hippocampus using the optical fractionator method of stereology as previously described (Kabadi et al., 2012).

Statistical analysis—Analysis was performed using the Sigmaplot Software (version 12). If the data passed a normality test, further analysis involved one-way ANOVA followed by multiple pairwise comparisons using Student-Newman-Keuls post-hoc test. If the data failed the normality test, further analysis involved non-parametric Kruskal-Wallis one-way ANOVA followed by multiple pairwise comparisons using Dunn's post hoc test.

Results miR-24-3p and miR-27a-3p are down-regulated and Bcl-2 family pro-apoptotic molecules are up-regulated in the injured cortex after TBI—To characterize the miR-23a-27a-24-2 cluster changes following TBI, miRs expression was profiled by GeneChip miRNA array in the cortex of controlled cortical impact (CCI) mice. These data indicated that TBI down-regulated the miR-23a~27a~24-2 cluster (data not shown). To confirm these changes a detailed expression profile analysis was performed of the members of this cluster using qPCR, and a rapid down-regulation of miR-23a-3p and miR-27a-3p was observed starting as early as 1 h after injury and lasting up to 24 h, followed by recovery at 72 h post-injury (FIG. 1A). In contrast, qPCR analysis showed no significant changes after TBI in the expression profiles of miR-24, the other member of the miR-23a~27a~24-2 cluster, or in the expression of the paralog cluster miR-23b~27b~24-1 (data not shown).

The mRNA expression levels for various Bcl-2 family pro-apoptotic proteins were analyzed in the cortex at different time points after TBI. qPCR demonstrated rapid up-regulation of the BH3-only family members Noxa (FIG. 1B), Bid and Bim (data not shown), with peak levels at 6 h post-injury, followed by a progressive decrease toward normal levels at 24 h post-injury. PUMA mRNA reached its peak at 1 h post-injury (FIG. 1B), and Bak mRNA (a pro-apoptotic multi-BH domain member) reached its peak at 1 h post-injury and remained elevated thereafter (data not shown).

Figure 2:
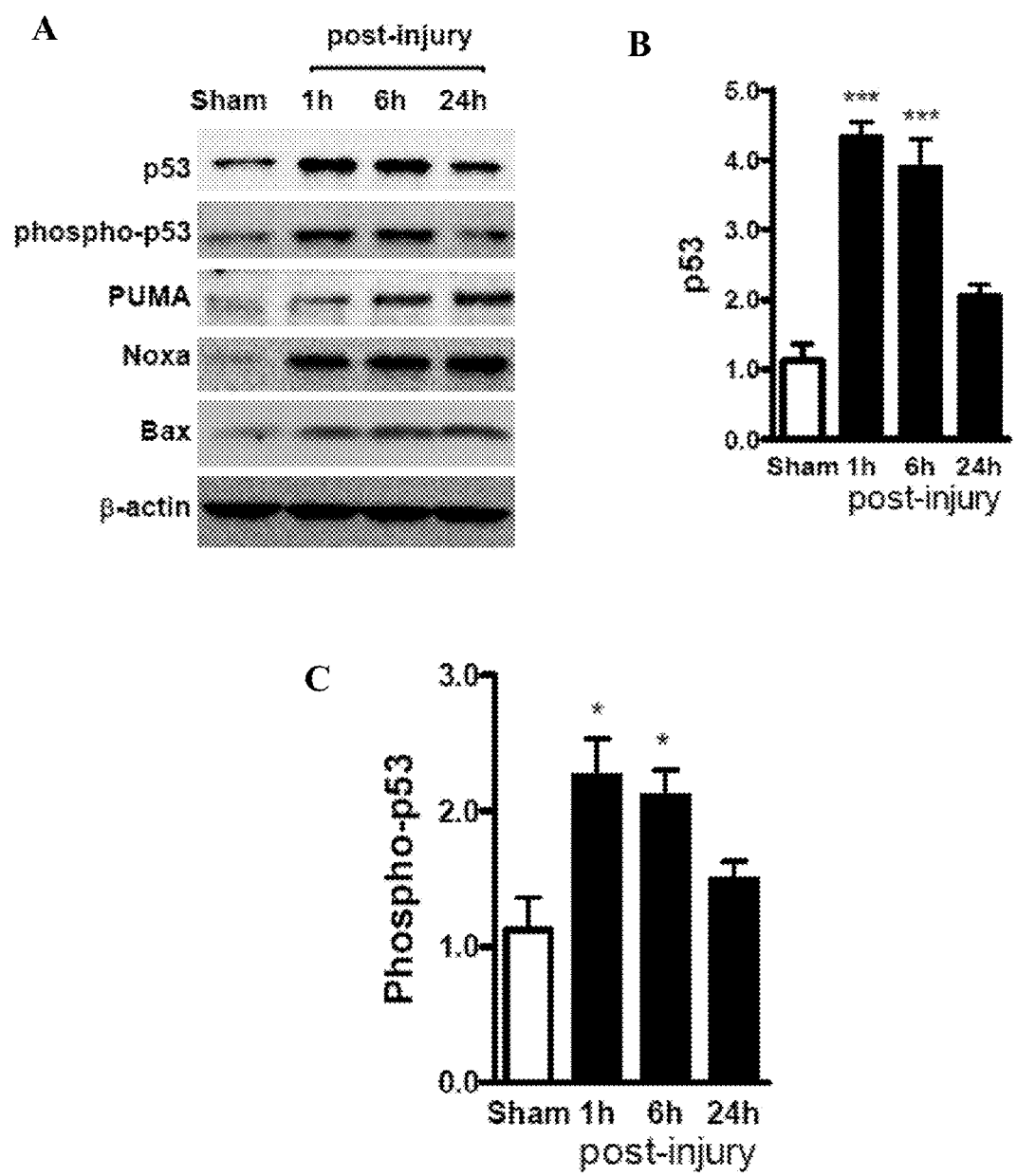
FIG. 2 shows activation of p53 and increased protein expression of pro-apoptotic Bcl-2 molecules after TBI. (A)Western blot analysis of the level of pro-apoptotic proteins in mouse injured cortex after TBI. Tissue lysates were fractioned on SDS-polyacrylamide gel and immunobloted with antibodies against p53, phosphorylated p53 (Ser 15), PUMA, Noxa, Bax and β-actin. Levels of p53 (B), phosphorylated p53 (Ser 15)(C), PUMA (D), Noxa (E) and Bax (F) were quantified as fold change to control levels after measurement of band intensity by densitometry and normalization to levels of β-actin. Data represent the mean± S.D. *-P<0.05; -P<0.01; *-P<0.001 vs. sham (N=4). Analysis by one-way ANOVA followed by multiple pairwise comparisons using Student-Newman-Keuls post-hoc test.
Figure 2:
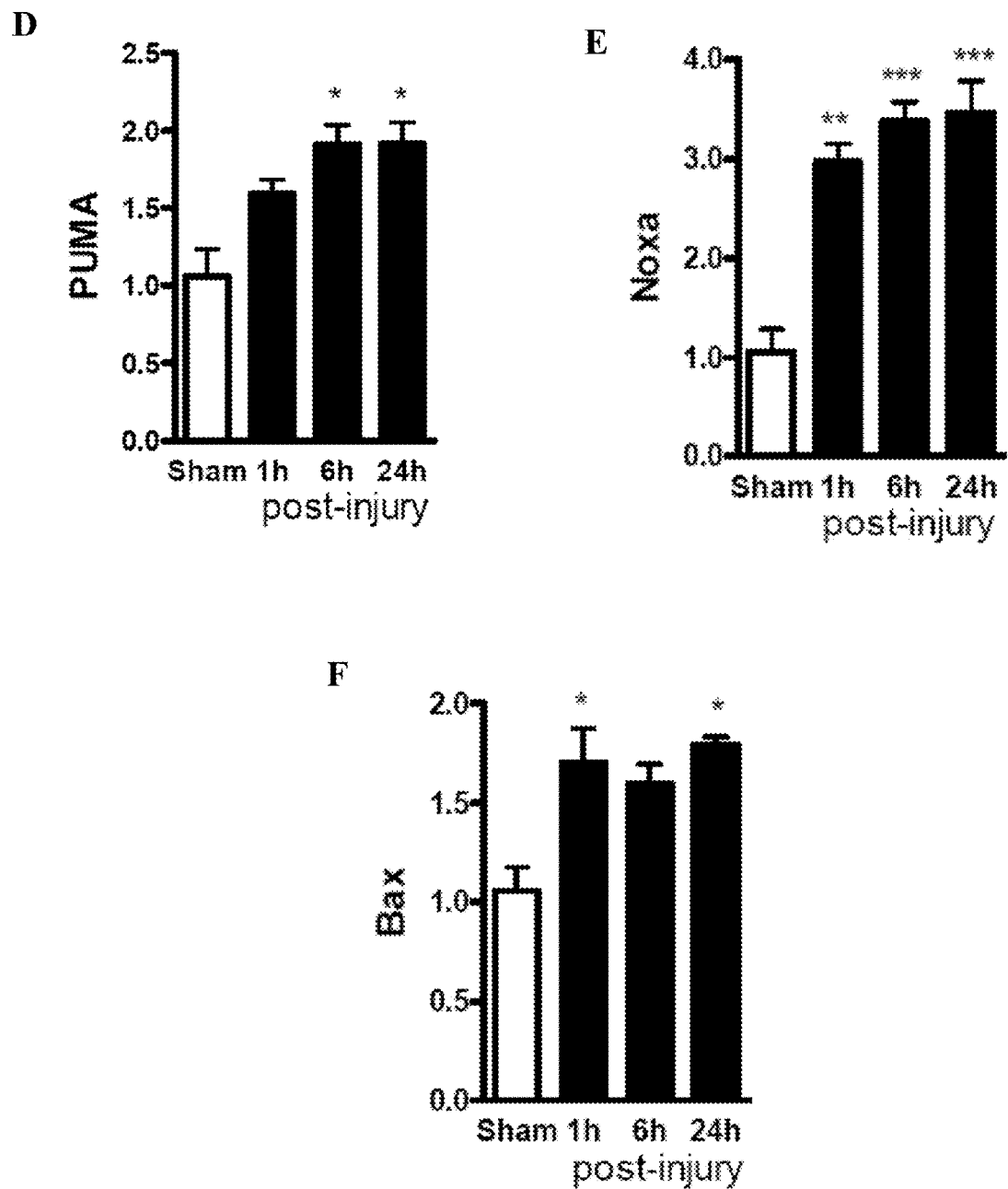

The mRNA data were corroborated by quantitative determination of protein levels of several key pro-apoptotic proteins using Western blot. The protein levels of total and phosphorylated (activated) p53, a key regulator of pro-apoptotic Bcl2 family (Vousden, 2005), increased rapidly and reached their peak at 1 h post-injury and decreased toward control levels at 24 h post-injury (FIG. 2). The protein levels of BH3-only proteins Noxa and Puma reached their peak at 6 h post-injury and remained elevated at 24 h post-injury (FIG. 2). The protein levels of the pro-apoptotic multi-BH domain protein Bax were significantly increased as early as 1 h post-injury and remained elevated through 24 h post-injury (FIG. 2).

Figure 3:
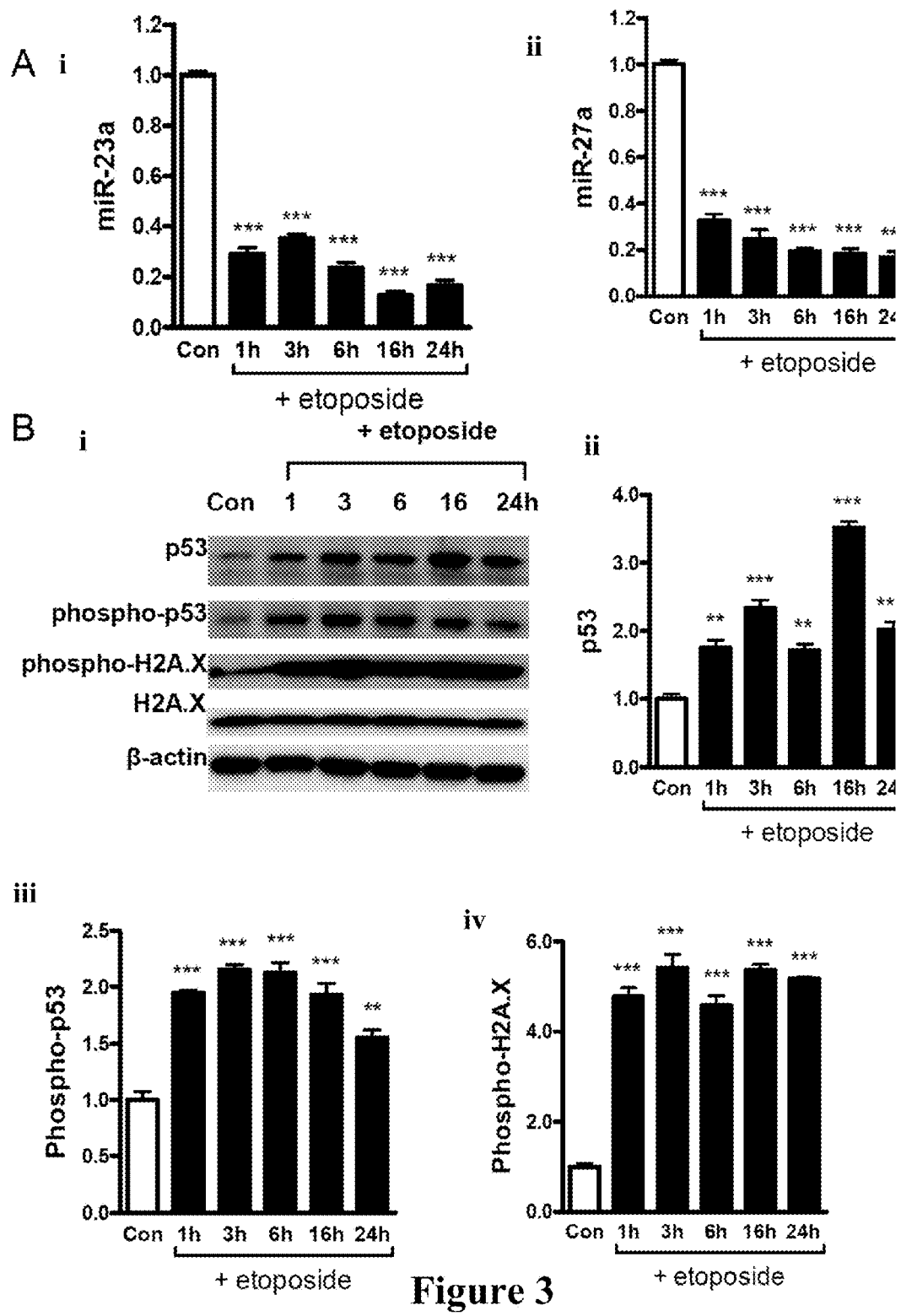
FIG. 3 shows miR-24-3p and miR-27a-3p down-regulation in an in vitro model of etoposide-induced neuronal apoptosis is associated with DNA damage, and increased expression and activation of p53 in primary cortical neurons. (A) qPCR quantification of miR-23a-3p (i) and -27a-3p(ii) expressions in rat cortical neurons (RCN) at different time points after etoposide treatment. Levels of miRs were normalized to U6 snRNA. Neuronal apoptosis were induced by etoposide as described above. Data represent the mean± S.D. *-P<0.05; -P<0.01; *-P<0.001 vs. control untreated RCN (N=4). (B) (i) Western blot analysis of the level of p53 and phosphorylated p53 in primary cortical neurons at different time points after etoposide treatment. Cell lysates were fractioned on SDS-polyacrylamide gel and immunobloted with antibodies against p53, phosphorylated p53 (Ser 15), histone H2A.X, phosphorylated histone H2A.X (Ser 139) and β-actin. Levels of p53 (ii), phosphorylated p53 (Ser 15) (iii), and phosphorylated histone H2A.X (Ser 139) (iv) were quantified as fold change to control levels after measurement of band intensity by densitometry and normalization to levels of β-actin. Data represent the mean±S.D. *-P<0.05; -P<0.01; *-P<0.001 vs. control untreated RCN (N=4). Analysis by one-way ANOVA followed by multiple pairwise comparisons using Student-Newman-Keuls post-hoc test.

No significant changes were observed in XIAP expression at mRNA or protein level after TBI in male mice (data not shown). In addition, qPCR analysis demonstrated that expression of some of predicted miR-23a-3p and -27a-3p targets involved in apoptosis pathways, such as MAP4K4, MAP2K7, calpain-6 and -7, were down-regulated after TBI (data not shown).

miR-24-3p and miR-27a-3p are down-regulated and p53 is activated in an in vitro model of etoposide-induced neuronal apoptosis—To explore the putative mechanisms of miR regulation of cell death, an in vitro model was used of etoposide-induced primary cortical neuron apoptosis (Sabirzhanov et al., 2012). Levels of miR-24-3p and miR-27a-3p were analyzed by qPCR at different time points after etoposide treatment. The data demonstrate significant reduction in levels of both miR-24-3p and miR-27a-3p compared to control. Both miRs were down-regulated rapidly, as early as 1 h after etoposide treatment (FIG. 3A). Quantitative Western blot analysis demonstrated a rapid (1 h) and sustained elevation in p53 expression and p53 phosphorylation on Ser 15 (markers of activation of the p53 pathways), as well as phosphorylated histone H2A.X (Ser 139), a marker of DNA damage (FIG. 3B). Similar to the TBI data, no changes were observed in expression of miR-24 or in the expression of the paralog cluster miR-23b~27b~24-1 after etoposide treatment (data not shown). The expression of miR-23-3p and -27a-3p in primary microglia and astrocytes was at least 100 times smaller compared to primary neurons (data not shown).

Figure 4:
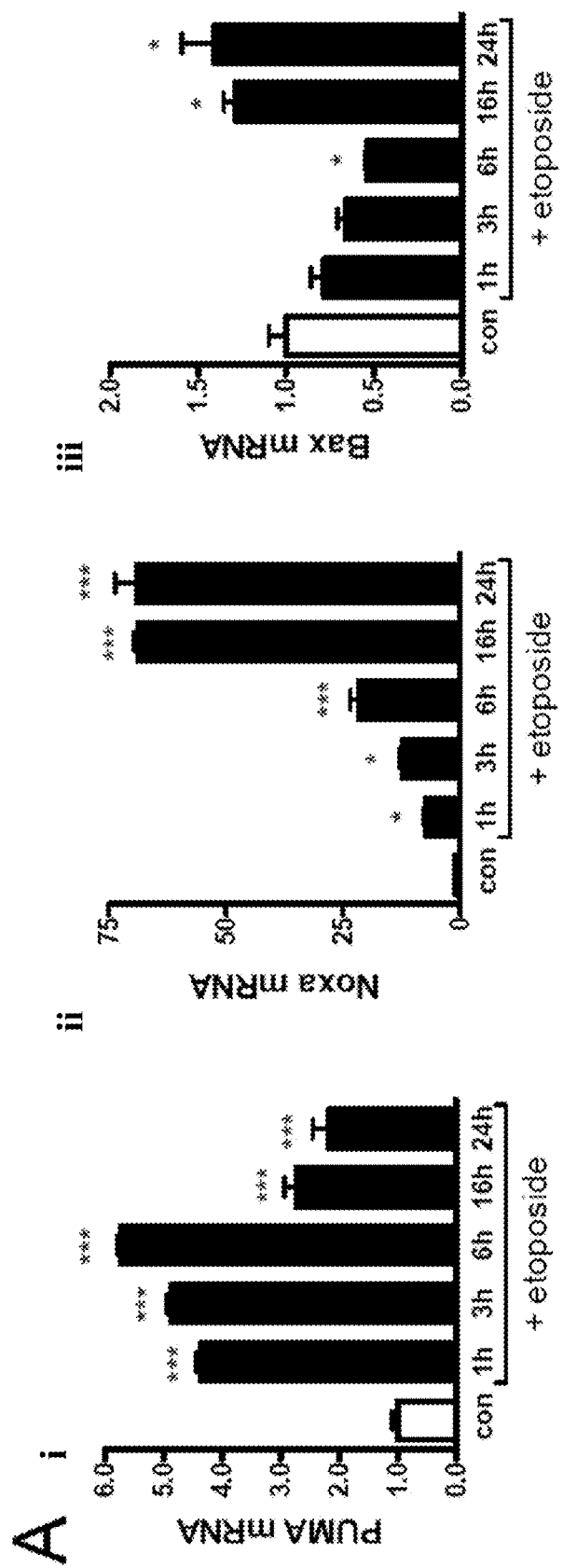
FIG. 4 shows mRNA and protein levels of pro-apoptotic members of Bcl-2 family were increased in etoposide-treated primary cortical neurons. (A) qPCR quantification of expression of pro-apoptotic genes: PUMA (i), Noxa (ii), and Bax (iii) in primary cortical neurons at different time points after etoposide treatment. Level of gene expression was normalized to GAPDH expression. Neuronal apoptosis were induced by etoposide as described above. Data represent the mean±S.D. *-P<0.05; -P<0.01; *-P<0.001 vs. control untreated RCN (N=4). (B) (i) Western blot analysis of the level of pro-apoptotic proteins in primary cortical neurons at different time points after etoposide treatment. Cell lysates were fractioned on SDS-polyacrylamide gel and immunoblotted with antibodies against PUMA, Noxa, Bax, active Bax and β-actin. Levels of PUMA(ii), Noxa (iii), Bax (iv) and active Bax (v) were quantified as fold change to control levels after measurement of band intensity by densitometry and normalization to levels of β-actin. Data represent the mean±S.D. *-P<0.05; -P<0.01; *-P<0.001 vs. control untreated RCN (N=4). Analysis by one-way ANOVA followed by multiple pairwise comparisons using Student-Newman-Keuls post-hoc test.
Figure 4:
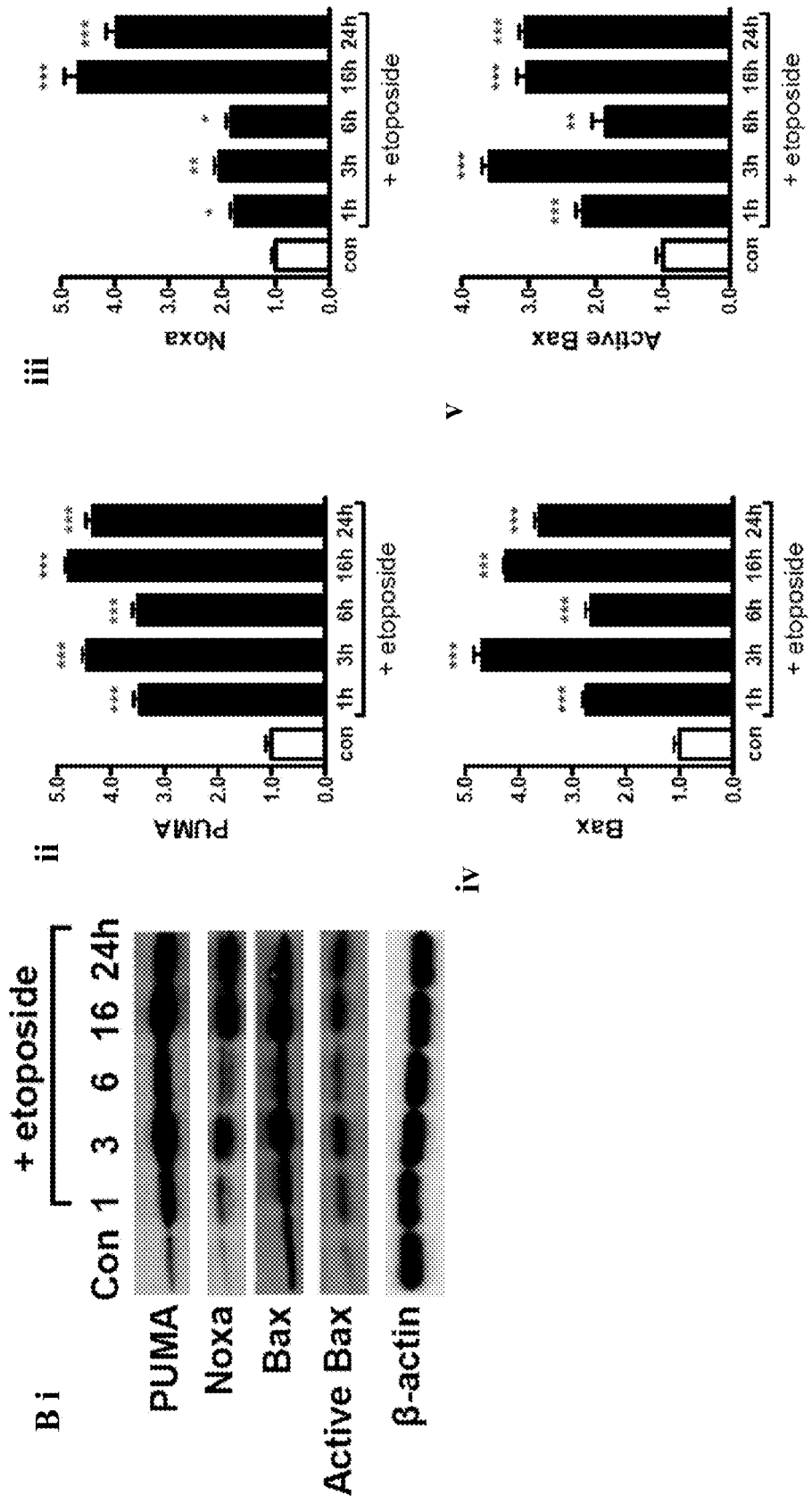

Pro-apoptotic members of Bcl-2 family are up-regulated in etoposide-treated primary cortical neurons—Some of the most important pathways induced by p53 activation involve pro-apoptotic members of Bcl-2 family. qPCR analysis demonstrated increased gene expression of pro-apoptotic members of Bcl-2 family such as Puma, Noxa, Bax (FIG. 4A) and Bim (data not shown) after etoposide treatment compared to control samples. The expression of Puma showed the earliest increase (1 h), reached a peak at 6 h, and declined at later time points. The expression of Noxa also increased rapidly and continued on an upward slope until 16-24 h. In contrast, gene expression of Bim (data not shown) and Bax showed significant increases only at 16-24 h. Quantitative Western blot analysis demonstrated that the protein levels of Puma, Noxa, Bax (FIG. 4B) and Bim (data not shown) were increased with a temporal profile similar, albeit not always identical, to the gene expression. Furthermore, the protein level of active Bax (FIG. 4B), as well as Bak (data not shown), was also increased by etoposide treatment.

Figure 5:
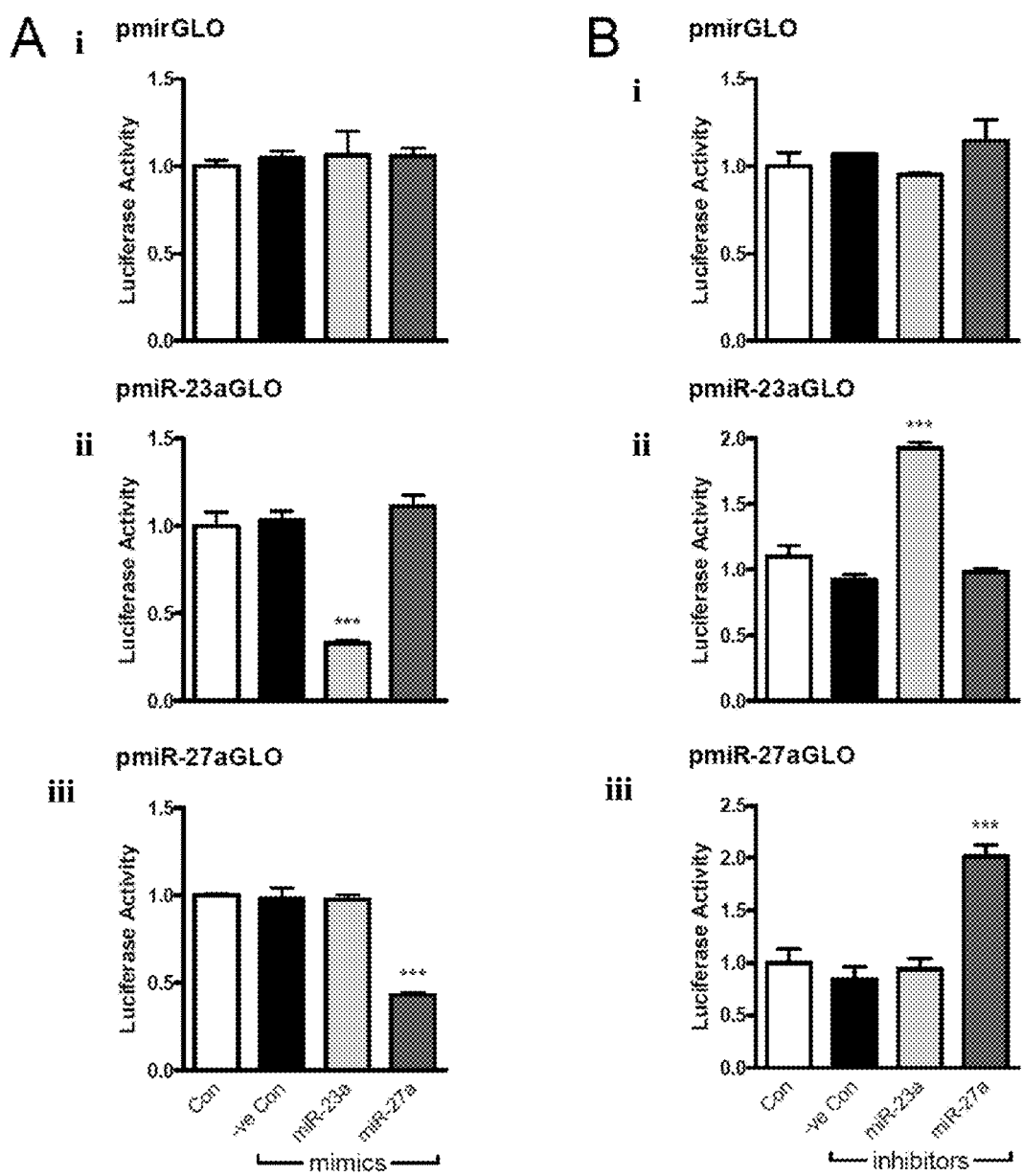
FIG. 5 shows that miR-23a-3p and -27a-3p mimics simulate endogenous miR-23a-3p and-27a-3p. RCN were transfected with either control vector (pmirGLO) or pmirGLO harboring both miR-23a-3p (pmiR-23aGLO) or miR-27a-3p (pmiR-27aGLO) target sequences and co-transfected with miR mimics or hairpin inhibitors. Twenty four hours after transfection cells were analyzed for luciferase activity. Normalized luciferase activities were shown as the percentage relative to the control cells transfected with only reporter plasmid. (A) RCN were co-transfected with pmirGLO (i) or pmiR-23aGLO (ii) or pmiR-27aGLO (iii) and miR-R23a-3p, -R27a-3p or negative control (-ye Con) mimics. (B) RCN were co-transfected with pmirGLO (i) or pmiR-23aGLO (ii) or pmiR-27aGLO (iii) and miR-R23a-3p, -R27a-3p or negative control (-ye cnt) miR hairpin inhibitor. Data represent the mean±S.D. *-P<0.001 vs. control cells (N=3). RCN were transfected with miR-R23a-3p, -R27a-3p or negative control (-ye Con) mimics and treated with etoposide as described above. (C) Analysis of qPCR data for miR-23a-3p (i) and-27a-3p (ii) expression 24 hours after etoposide treatment, normalized to U6 snRNA (N=4). Data are expressed as percentage of control etoposide untreated neurons. Data represent the mean±S.D. *-P<0.001 vs. untreated neurons; +++-P<0.0)1; vs. negative control (-ye cnt) miR mimic transfected, etoposide treated RCN. Analysis by one-way ANOVA followed by multiple pairwise comparisons using Student-Newman-Keuls post-hoc test.
Figure 5:
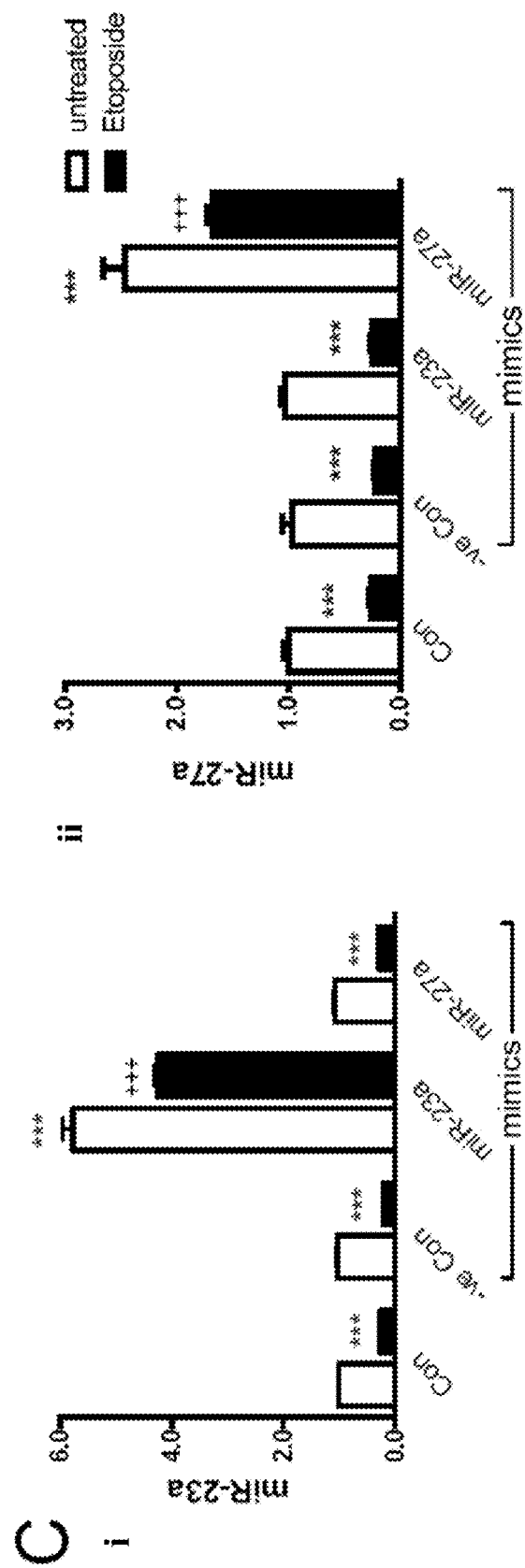

Similar to TBI data, no significant changes were observed in XIAP expression after etoposide treatment (data not shown). Down-regulation of MAP4K4, MAP2K7, calpain-6 and -7 was observed after etoposide treatment compared to control samples (data not shown).

miR-23a-3p and -27a-3p mimics compensate for the decrease of endogenous miR-23a-3p, -27a-3p in etoposide-treated primary cortical neurons. To validate the ability of miR mimics to specifically replicate the function of endogenous miRs, RCN were co-transfected with either control vector (pmirGLO) or pmirGLO harboring either mi-R23a-3p (pmiR-23aGLO) or mi-R27a-3p (pmiR-27aGLO) target sequences and miR-R23a-3p, -R27a-3p or negative control mimics. Twenty four hours after transfection neurons were analyzed for luciferase activity. As predicted, none of miR mimics affected luciferase activity in neurons transfected with control vector (FIG. 5A). Relative luciferase activity in neurons co-transfected with the pmiR-23aGlo and miR-23a mimic was 3 times lower compared to cells transfected with pmiR-23aGlo only. Neither miR-27a-3p nor negative control microRNA mimics effected luciferase activity in neurons transfected with pmiR-23aGLO (FIG. 5A). Relative luciferase activity in neurons co-transfected with the miR-27a-3p mimic and pmiR-27aGLO was 2.35 times lower compared to cells transfected with just pmiR-27aGlo. miR-23a-3p and negative control microRNA mimics did not affect luciferase activity in Luciferase activity in neurons transfected with pmiR-27aGLO (FIG. 5A). microRNA hairpin inhibitors are single-stranded RNA oligonucleotides designed to bind to and sequester the complimentary mature microRNA strand and prevent binding of miRs to their mRNAs targets, thereby blocking their activity. To validate the activity and specificity of microRNA hairpin inhibitors, RCN were co-transfected with either control vector-pmirGLO, pmiR-23aGLO or pmiR-27aGLO and miR-R23a-3p, -R27a-3p or negative control microRNA hairpin inhibitors. None of miR hairpin inhibitors affected luciferase activity in neurons transfected with control vector -pmirGLO (FIG. 5B). Relative luciferase activity in neurons co-transfected with the pmiR-23aGlo and miR-23a hairpin inhibitor was 2 times higher compared to cells transfected with just pmiR-23aGlo. Neither miR-27a-3p nor negative control microRNA mimics effected luciferase activity in neurons transfected with pmiR-23aGLO (FIG. 5B). Luciferase activity 2 times higher in neurons co-transfected with miR-27a-3p hairpin inhibitor and pmiR-27aGLO compared to cells transfected with pmiR-27aGlo only. miR-23a-3p and negative control microRNA mimics did not affect luciferase activity in neurons transfected with pmiR-27aGLO (FIG. 5B).

To test the hypothesis that miR-23a-3p and miR-27a-3p decline plays a significant role in etoposide-induced neuronal apoptosis, primary cortical neurons were transfected with miR-23a-3p and miR-27a-3p mimics prior to etoposide treatment. These mimics are intended to compensate for the decline in endogenous miR-23a-3p and miR-27a-3p levels. The level of miR-23a in control neurons transfected with the miR-23a mimic was 5.7 times increased compared to untransfected control cells; the level of miR-23a in etoposide treated neurons transfected with the miR-23a mimic was 4.25 times increased compared to untransfected control cells, more than compensating for the etoposide-induced decline in endogenous miR (FIG. 5C). The level of miR-27a in neurons transfected with the miR-27a mimic was 2.5 times increased compared to untransfected control cells; the level of miR-27a in etoposide treated neurons transfected with the miR-27a mimic was 1.69 times higher compared to untransfected control cells, more than compensating for the etoposide-induced decline in endogenous miR (FIG. 5C). Importantly, attenuation of miR23a and -27a decline by transfection with the miR-24-3p or miR-27a-3p mimics significantly reduced etoposide-induced neuronal cell death (LDH assay) compared to mock transfection and microRNA mimic negative controls (FIG. 6A). Similarly, etoposide-induced caspase-3 activity was significantly reduced in neurons transfected with miR-24-3p or miR-27a-3p mimics compared to mock transfection and microRNA mimic negative controls (FIG. 6B). These data indicate that miR-23a and -27a are negative regulators of neuronal apoptosis.

Figure 6:
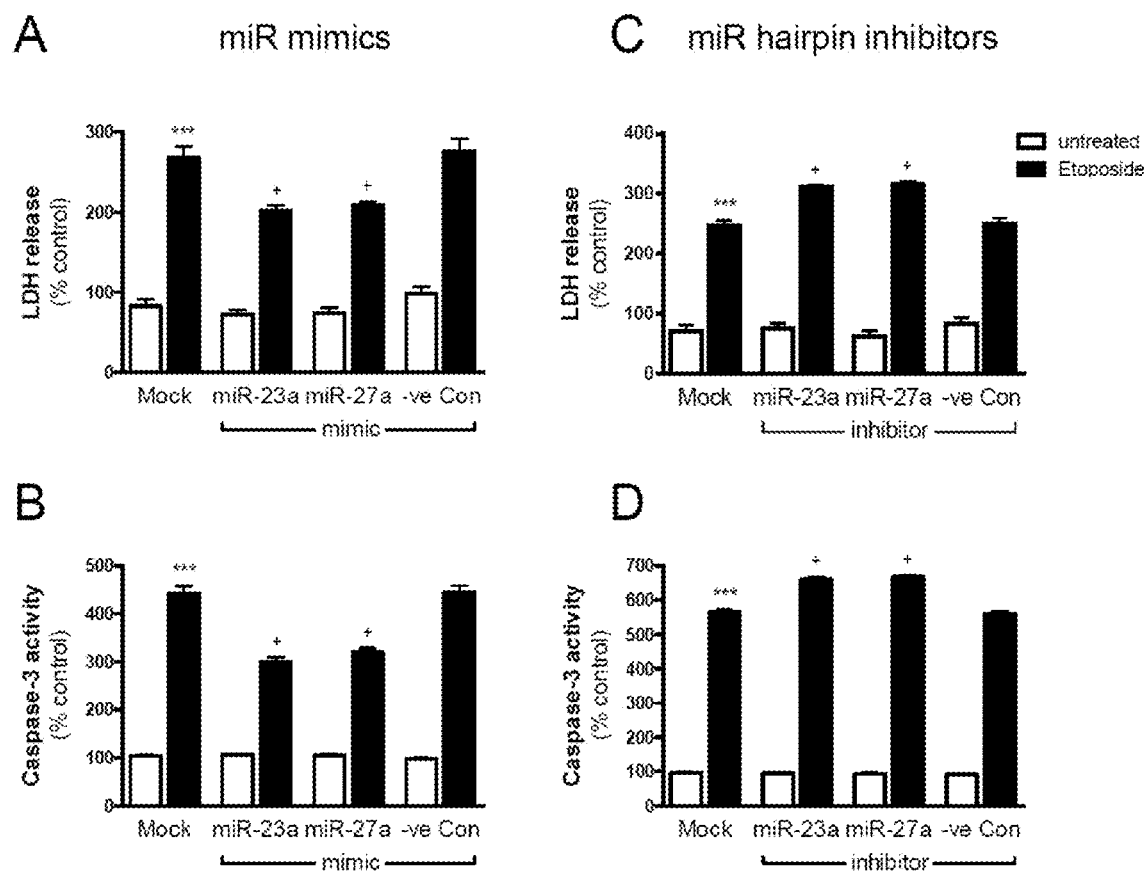
FIG. 6 shows that miR-23a and -27a mimics attenuate neuronal apoptosis and caspase-3 activation in etoposide-treated primary cortical neurons while transfection with miR-23a and -27a hairpin inhibitors have opposite effects. Transfection of RCN with miR-23a-3p and -27a-3p mimics significantly decreased etoposide-induced LDH release in in rat cortical neuronal cultures (A). Neurons were transfected with miR-23a-3p and miR-27a-3p mimics or negative control miR mimic (-ye Con mimic) and 4 h later treated with etoposide as described above. LDH release was measured after 24 h of treatment. Histograms indicate LDH release as percentage of control untreated RCN. Transfection of RCN with miR-23a-3p and -27a-3p 3p attenuates caspase-3 activation in etoposide-treated primary cortical neurons (B). RCN were transfected and etoposide treated as described above. Caspase-3-like activity was assayed fluorometrically by measuring the accumulation of free AMC resulting after cleavage of Ac-DEVD-AMC. Data are expressed as percentage of control untreated neurons. Transfection of RCN with miR-23a-3p and -27a-3p hairpin inhibitors increased etoposide-induced LDH release in in rat cortical neuronal cultures (C). Transfection of RCN with miR-23a-3p and -27a-3p 3p hairpin inhibitors enhanced caspase-3 activation in etoposide-treated primary cortical neurons (D). RCN were transfected and etoposide treated as described above. Caspase-3-like activity was assayed fluorometrically by measuring the accumulation of free AMC resulting after cleavage of Ac-DEVD-AMC. Data are expressed as percentage of control etoposide treated neurons. Data represent the mean±S.D. *-P<0.05; -P<0.01; *-P<0.001 vs. mock untreated RCN; +-P<0.05; ++-P<0.01; vs. etoposide treated mock (N=4), N=8 cultures per condition. Analysis by one-way ANOVA followed by multiple pairwise comparisons using Student-Newman-Keuls post-hoc test.
Figure 7:
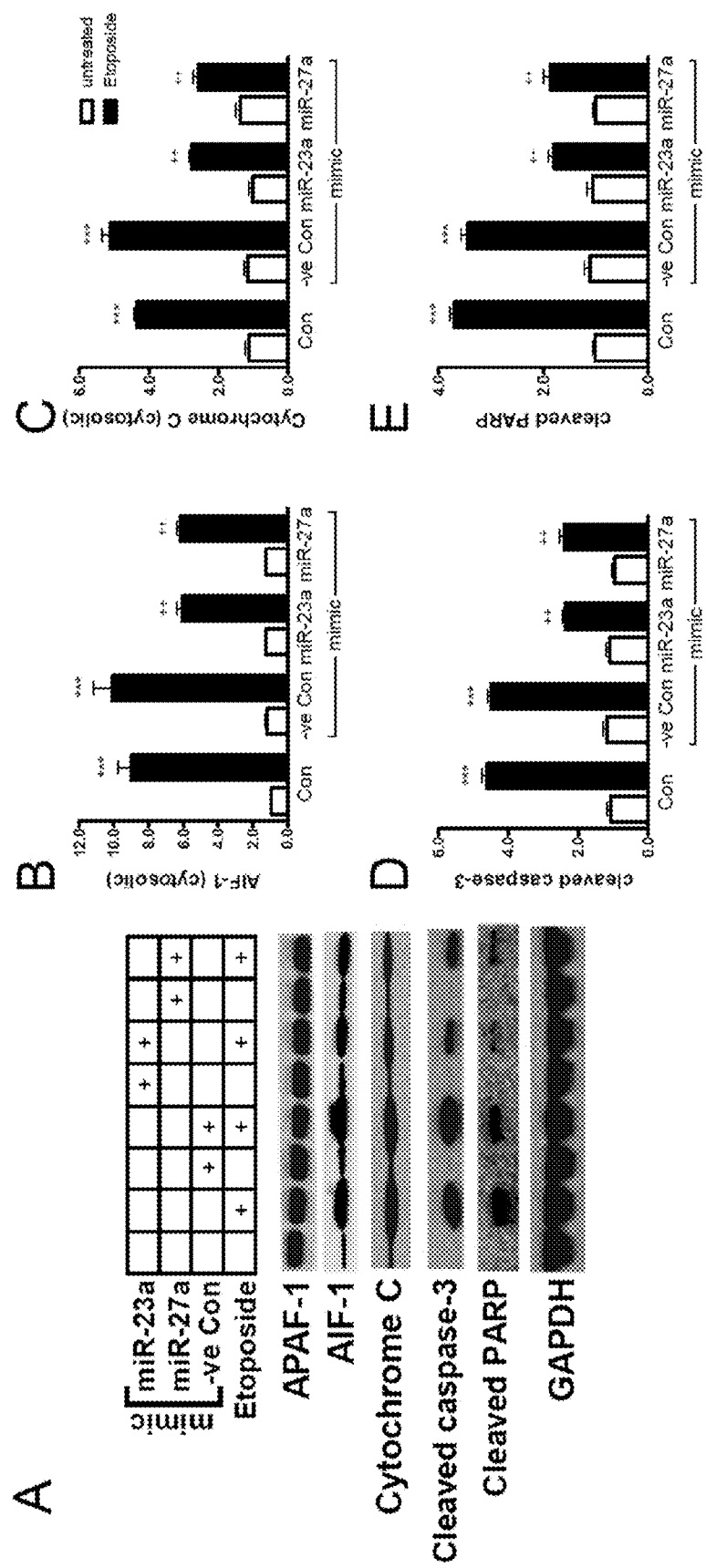
FIG. 7 shows miRs-23a and -27a mimics attenuate etoposide-induced release of AIF and cytochrome c into the cytosol as well as cleavage (activation) of caspase-3, PARP and α-Fodrin. Transfection of RCN with miRs 23a and -27a decrease the levels of AIF-1, Cytochrome C and cleaved of caspase-3 and PARP in cytosolic fraction of etoposide-treated primary cortical neurons. Neurons were transfected with miR-23a-3p and miR-27a-3p mimics and 4 h later treated with etoposide as described above. Cytosolic fractions were fractioned on SDS-polyacrylamide gel and immunoblotted with antibodies against AIF-1, Cytochrome C, cleaved caspase-3, PARP and GAPDH and β-actin (A). Levels of AIF-1(B), Cytochrome C (C) and cleaved caspase-3 (D) and PARP (E) proteins in cytosolic fraction of RCN were quantified as fold change to levels control etoposide treated cell after measurement of band intensity by densitometry. Data represent the mean±SD. *p<0.05, p<0.01, *P<0.001 versus mock untreated RCN; ++-P<0.01; vs. etoposide treated mock (n=4). Whole cell lysates were fractioned on SDS-polyacrylamide gel and immunoblotted with antibodies against α-Fodrin and β-actin (Fi). Level of α-fodrin and products of its cleavage were quantified as fold change to control RCN level after measurement of band intensity by densitometry and normalization to /levels of β-actin (F). (ii) α-fodrin 240 kDA, (iii) α-fodrin 145 kDA, (iv)a-fodrin 120 kDA. Data represent the mean±S.D. *-P<0.05 vs. mock untreated RCN; +-P<0.05; vs. etoposide treated mock (n=4). Analysis by one-way ANOVA followed by multiple pairwise comparisons using Student-Newman-Keuls post-hoc test.
Figure 7:
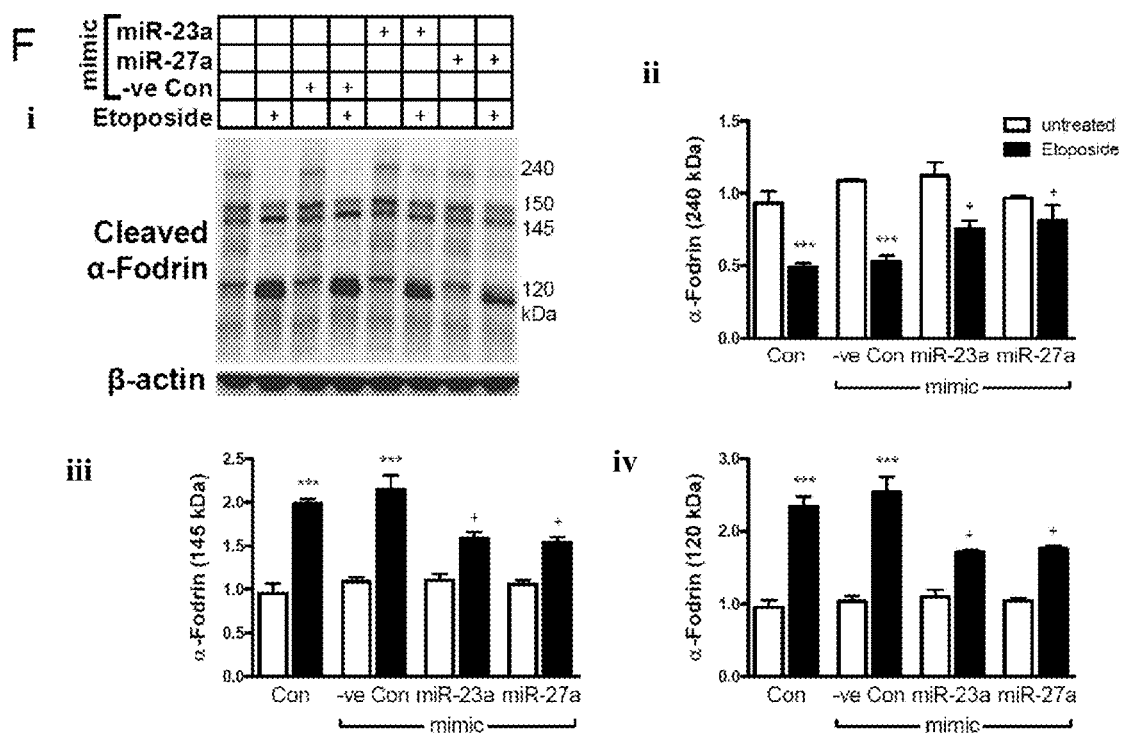
Figure 8:
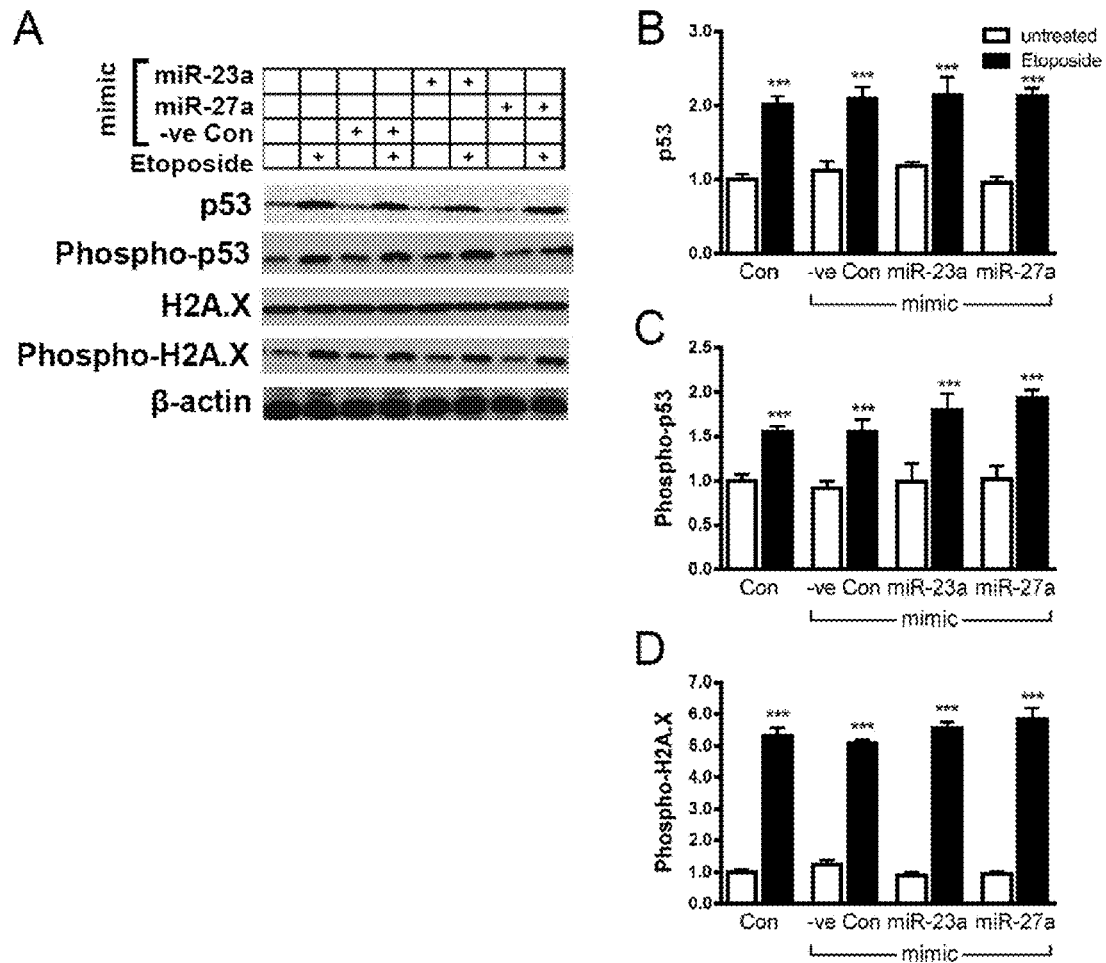
FIG. 8 shows that miR-23a and -27 do not alter etoposide-induced p53 activation or histone H2A.X phosphorylation. Neurons were transfected with miR-23a-3p and miR-27a-3p mimics and 4 h later treated with etoposide as described above. Whole cell lysates were fractioned on SDS-polyacrylamide gel and immunobloted with antibodies against p53, phosphorylated p53 (Ser 15), histone H2A.X, phosphorylated histone H2A.X (Ser 139) and β-actin (A). Level of p53 (B), phosphorylated p53 (C) and phosphorylated histone H2A.X (D) were quantified as -fold change to control RCN level after measurement of band intensity by densitometry and normalization to levels of β-actin. Data represent the mean±SD. *p<0.05, p<0.01, *P<0.001 versus control untreated RCN; +p<0.05, ++-P<0.01, +++P<0.001 vs. etoposide treated mock (n=4). (n=4). Analysis by one-way ANOVA followed by multiple pairwise comparisons using Student-Newman-Keuls post-hoc test.
Figure 9:
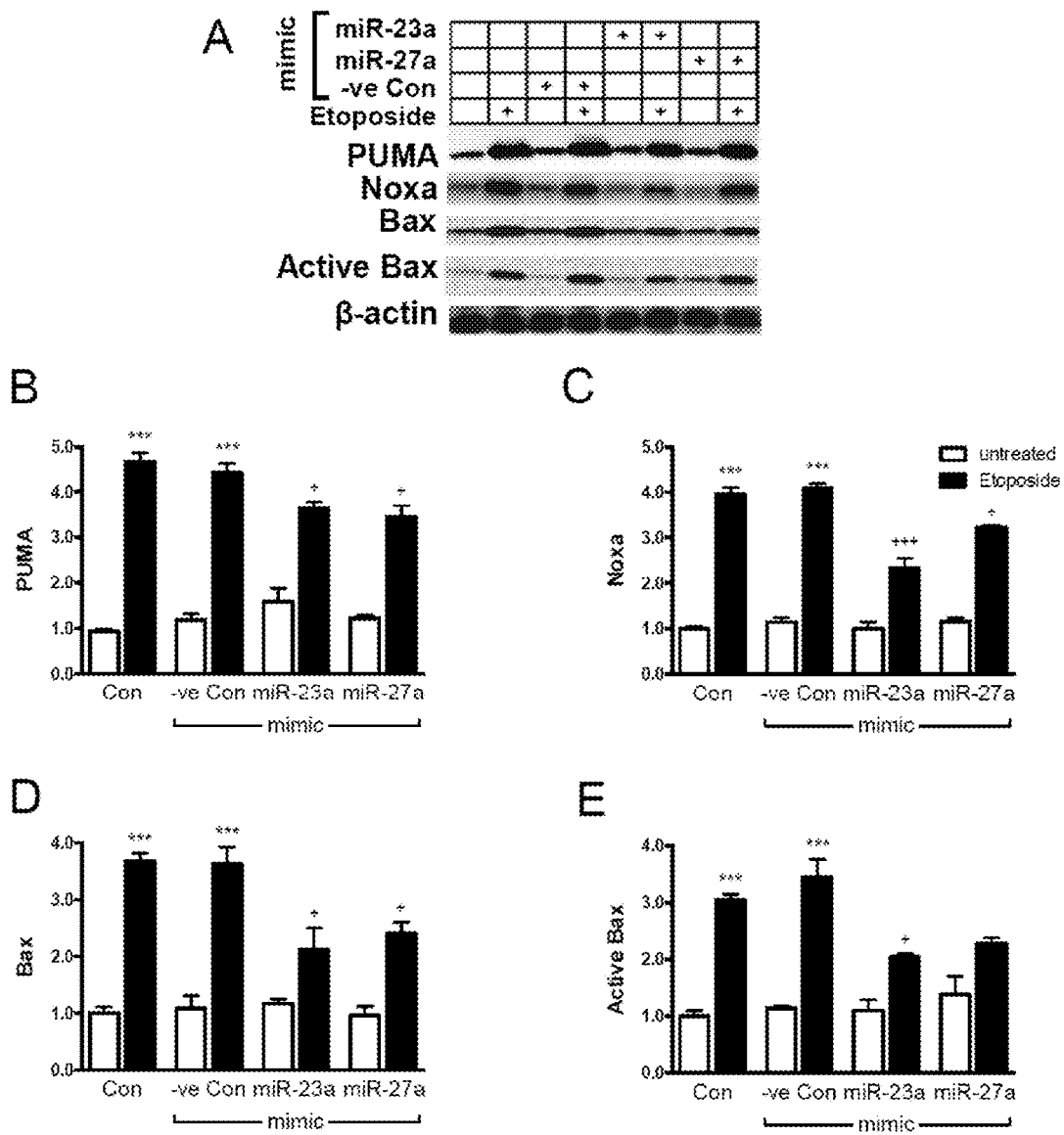
FIG. 9 shows that miR-23a and -27a mimics attenuate etoposide-induced expression of pro-apoptotic Bcl-2 family members. Neurons were transfected with miR-23a-3p and miR-27a-3p mimics and 4 h later treated with etoposide as described above. Whole cell lysates were fractioned on SDS-polyacrylamide gel and immunoblotted with antibodies against PUMA, Noxa, Bax, active Bax and β-actin (A). Level of PUMA (B), Noxa (C) Bax (D) and active Bax (E) were quantified as fold change to control RCN level after measurement of band intensity by densitometry and normalization to levels of β-actin. Data represent the mean±SD. *p<0.05, p<0.01, *P<0.001 versus mock untreated RCN; +p<0.05, ++-P<0.01, +++P<0.001 vs. etoposide treated mock (n =4). Analysis by one-way ANOVA followed by multiple pairwise comparisons using Student-Newman-Keuls post-hoc test.
Figure 10:
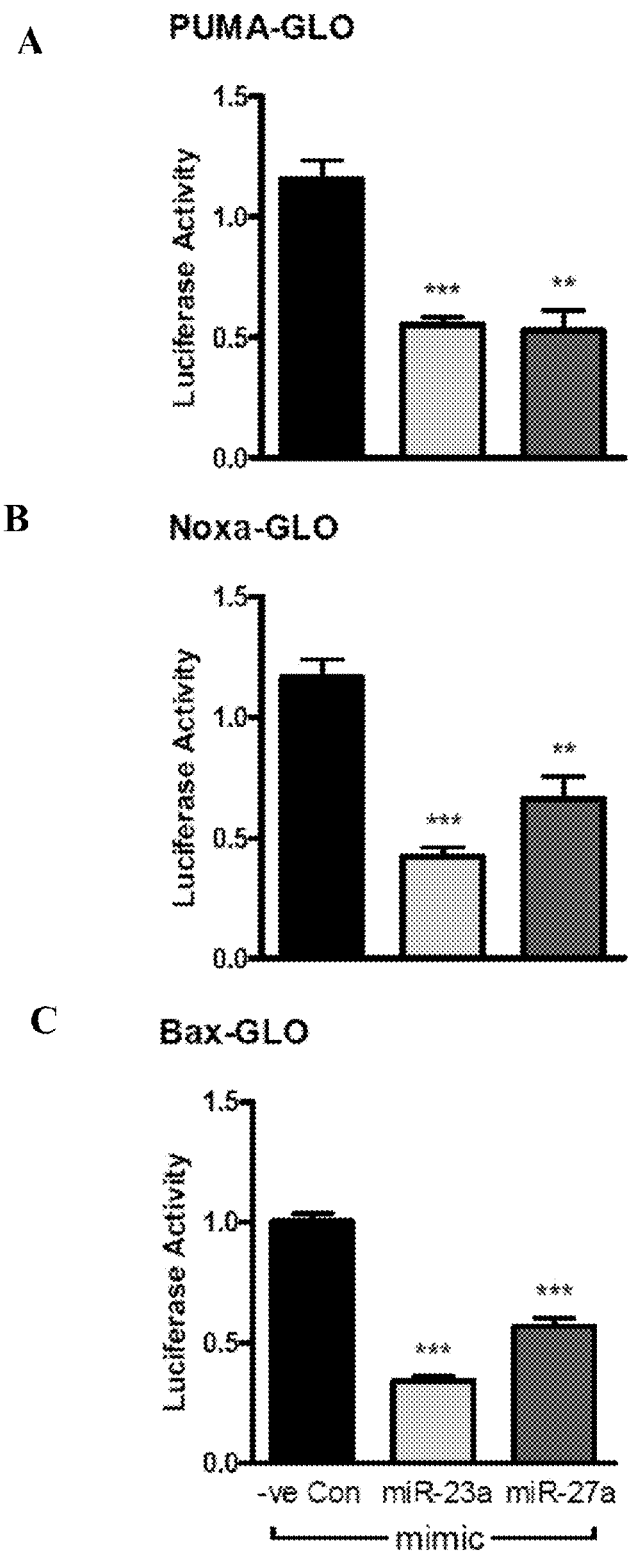
FIG. 10 shows that miR-23a and -27a target PUMA, Noxa and Bax. SH-SY5Y cells were transfected with either negative control miR (-ye cnt) or miR-23a-3p or -27a-3p mimics. Cells were also co-transfected with reporter plasmids with inserted 3' UTRs of mouse PUMA (A), Noxa (B) and Bax (C). Twenty four hours after transfection cells were analyzed for luciferase activity. Normalized luciferase activities were shown as the percentage relative to the cells transfected with reporter plasmid and -ve Con miR mimic, which was set as 1. Experiments were performed in triplicate. Data represent the mean±S.D. p<0.01, *p <0.001* (n=3). Analysis by one-way ANOVA followed by multiple pairwise comparisons using Student-Newman-Keuls post-hoc test.

The microRNA hairpin inhibitor approach was also used to confirm that decreased miR-24-3p and miR-27a-3p functional activity promotes neuronal apoptosis and caspase-3 activation after etoposide treatment. RCN cultures were transfected with miR-24-3p and miR-27a-3p hairpin inhibitors followed by treatment with etoposide. Importantly, a significant increase was observed in etoposide-induced neuronal cell death (LDH assay) and caspase-3 activity in cells transfected with miR-24-3p and miR-27a-3p hairpin inhibitors compared to mock transfection and microRNA hairpin inhibitor negative controls (FIG. 6 C, D). Transfection of neurons with miR-24-3p and miR-27a-3p hairpin inhibitors did not cause a significant induction of apoptosis in the absence of etoposide, suggesting that changes in these miRs are not sufficient on their own to cause neuronal cell death.

miR -23a and -27a mimics attenuate molecular mechanisms of neuronal apoptosis—One of the most important steps in apoptosis involves the release of cytochrome c and AIF from the mitochondria to initiate the intrinsic caspase activation pathway and a caspase-independent cell death pathway, respectively. To assess whether changes in miR-24-3p and miR-27a-3p act upstream of these events, cells transfected with miR mimics were examined. Quantitative Western blot analysis demonstrated that miR-24-3p and miR-27a-3p mimics, with or without etoposide treatment, did not show changes of protein levels for key pro-apoptotic proteins, including apoptotic peptidase activating factor 1 (APAF1), apoptosis-inducing factor, mitochondrion-associated 1 (AIF-1), cytochrome c and TNF receptor superfamily member 6 (Fas) in whole cell lysates (data not shown). Translocation of AIF and cytochrome c from mitochondria to cytoplasm is a well known marker of apoptotic cell death (Sabirzhanov et al., 2012). Analysis of cytosolic fractions revealed that miR-24-3p and miR-27a-3p mimics significantly reduced etoposide-induced release of AIF and cytochrome c into the cytosol (FIG. 7A, B, C). In addition, miR-24-3p and miR-27a-3p mimics significantly attenuated etoposide-induced cleavage of caspase-3 (FIG. 7A, D), as well as cleavage of PARP and a-Fodrin, well-known caspase substrates whose cleavage are a good indicator of caspase activity. Quantitative Western blot analysis demonstrated that neurons transfected with miR-24-3p and miR-27a-3p mimics displayed significantly reduced levels of the cleaved fragment of PARP (FIG. 7A, E), and significantly attenuated the decrease of the full length uncleaved fragment of a-Fodrin (240 kDa) (FIG. 7F) after etoposide treatment. In addition, neurons transfected with the mimics had significantly reduced levels of the levels of both calpain-dependent (150/145 kDa) and caspase-dependent cleavage (150/120 kDa) (Siman et al., 1984; Cryns et al., 1996; Siman et al., 2004) fragments of a-Fodrin after etoposide treatment (FIG. 7F).

miR-23a and -27 mimics act downstream of p53 activation—To explore at a molecular level the effect of miR-23a and -27a on DNA-damage induced p53-dependent cell death pathways, the effect of miR-23a and -27a mimics was analyzed on pathways downstream of p53 activation. Transfection of RCN by miR-24-3p and miR-27a-3p mimics did not attenuate etoposide-induced increases in phosphorylated histone H2A.X (Ser 139) or p53 protein levels expression and/or phosphorylation (FIG. 8).

miR-23a and -27a mimics attenuate expression of pro-apoptotic Bcl-2 family members during apoptosis—The protein levels of key pro-apoptotic members of Bcl-2 family was investigated in neurons transfected with miR-23-3p and miR-27a-3p mimics followed by etoposide treatment. Quantitative Western blot analysis demonstrated that the mimics significantly attenuated the etoposide-induced increase in PUMA, Noxa, Bax and active Bax levels (FIG. 9), but not Bim or BAK1 (data not shown) expression levels.

miR-23a and -27a target 3' UTRs of PUMA, Noxa and Bax. miRNA target prediction tools from mlRecords were used to predict mRNA targets for miR-23a and -27a (Seed parameter settings: Minimum seed size 7; Allow single G:U; Allow single mismatch). 16 sites for miR-23a-3p and 14 sites for miR-27a-3p were predicted in mouse Noxa 3'UTR (NCBI Reference Sequence: NM_021451.2); 4 sites for miR-23a-3p and 7 sites for miR-27a-3p were predicted in mouse PUMA 3'UTR (NCBI Reference Sequence: BC044782.2); 1 site for miR-23a-3p and 4 sites for miR-27a-3p were predicted in mouse Bax 3'UTR (NCBI Reference Sequence: BCO53380.1). To directly test whether miR-23a-3p and-27a-3p could functionally target PUMA, Noxa and Bax mRNAs, a luciferase reporter assay was used in which the 3' UTRs of mouse PUMA, Noxa and Bax, were inserted 3' of the firefly luciferase gene into pmirGLO plasmid. Each luciferase construct was co-transfected with either negative control, miR-23a-3p or -27a-3p microRNA mimics into SH-SY5Y cells, and luciferase activity was measured 24 hours after transfection. miR-23a-3p and -27a-3p, but not negative control miR mimic, significantly reduced luciferase activity in cells transfected with constructs containing 3' UTRs of PUMA, Noxa and Bax (FIG. 10). Together, these data demonstrate that miR-23a-3p or -27a-3p are capable of targeting sequences in the 3' UTRs of PUMA, Noxa and Bax mRNAs and inhibit expression of mRNA that include these sequences.

Figure 11:
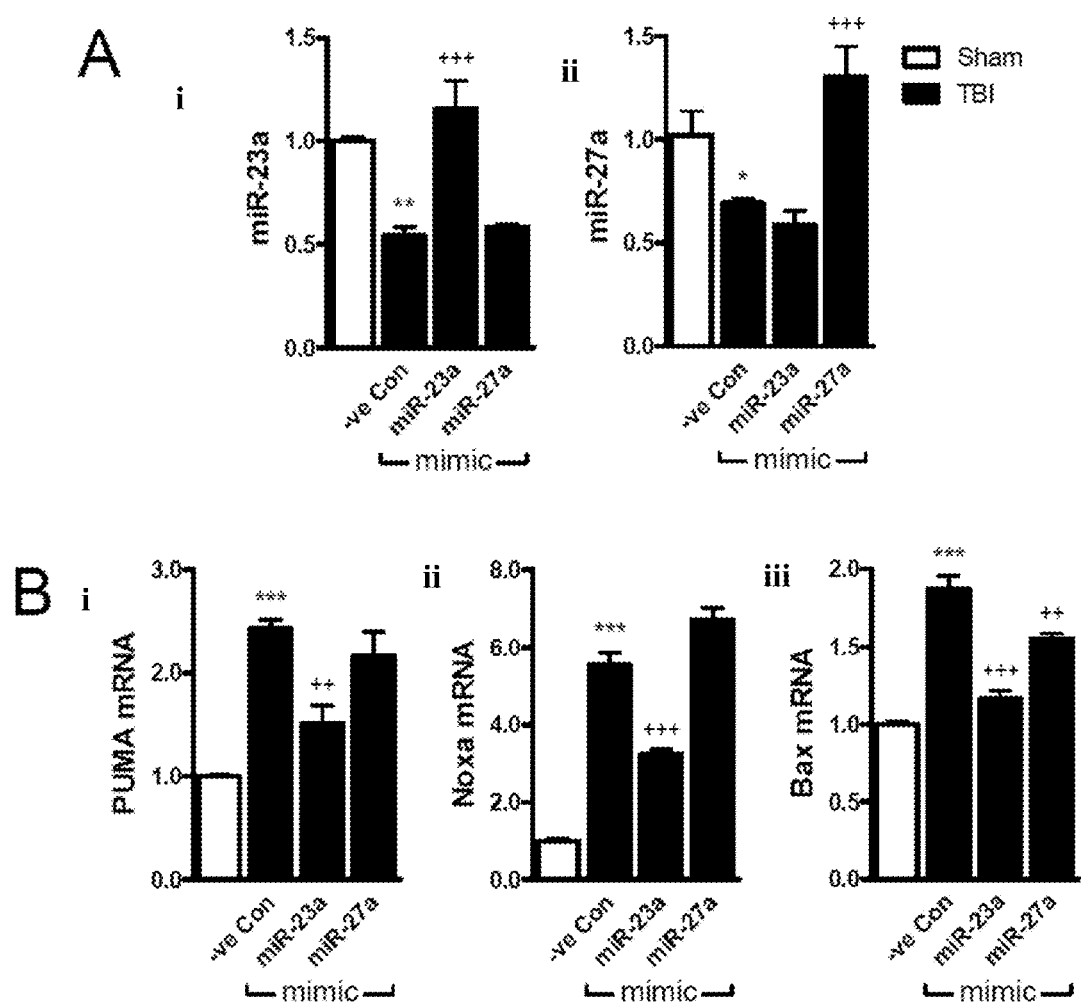
FIG. 11 shows that intracerebroventricular (icy) injection of miR-23a and miR-27a mimics attenuate expression of PUMA, Noxa and Bax in injured cortex after TBI. (A) qPCR quantification of miR-23a-3p (i), -27a-3p (II). (B) PUMA (i) Noxa (ii) and Bax (iii) expressions in mouse cortex 6 hours after TBI and icy injection of miR-23a-3p or -27a-3p or negative control miR (-ve Con) mimics. Levels of miRs were normalized to U6 snRNA; levels of PUMA, Noxa and Bax were normalized to GAPDH. Data represent the mean±S.D. *-P<0.05; -P<0.01; *-P<0.001 vs. sham animals; +-P<0.05; ++-P<0.01; vs. injured-ve Con injected group (N=4-6). (C i) Whole tissue lysates from mouse cortex 24 hours after TBI and icy injection of miR-23a-3p or -27a-3p or -ve cnt mimics were fractioned on SDS-polyacrylamide gel and immunobloted with antibodies against PUMA, Noxa, Bax, active Bax and β-actin. Levels of PUMA (ii), Noxa (iii), Bax (iv) and active Bax (v) in total lysates were quantified as fold change to the levels of sham after measurement of band intensity by densitometry. Data represent the mean±S.D. *-P<0.05; -P<0.01; *-P<0.001 vs. sham animals; +-P<0.05; ++-P<0.01; vs. injured-ve cnt injected group (N=4-6).
Figure 11:
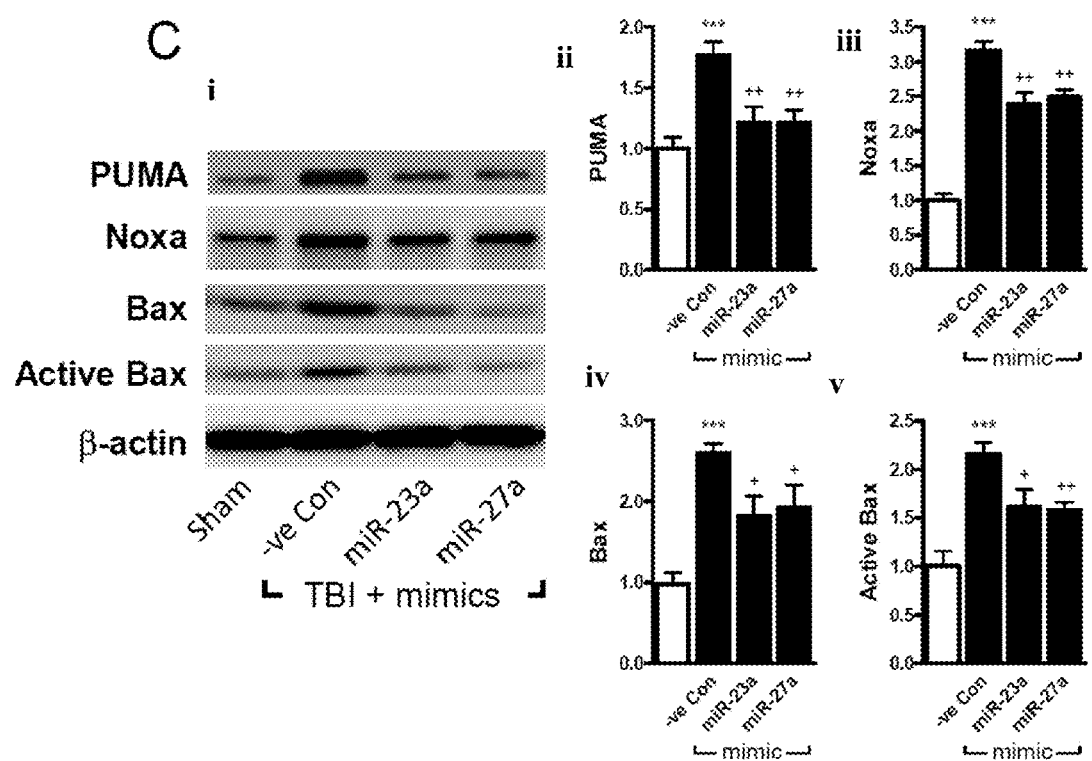

Intracerebroventricular (icv) injection of miR-23a and miR-27a mimics attenuate expression of PUMA, Noxa and Bax and markers of apoptosis after TBI. miR-23a-3p and -27a-3p mimics were administered after TBI and the expression of pro-apoptotic Bcl-2 family members was examined, including PUMA, Noxa and Bax. At 15 minutes post-injury, mice received a single icv injection of either miR-23a, miR-27a or negative control miR mimics. Levels of miR-23a-3p, -27a-3p, Puma, Noxa and Bax mRNA were analyzed by qPCR in the injured cortex 6 hours after TBI. The data demonstrated that injection of miR-23a and miR-27a mimics completely reversed the TBI-induced decline in miR-23a and miR-27a, respectively, compared to TBI mice injected with negative control miR mimic (FIG. 11A). Importantly, injection of miR-23a-3p and -27a-3p mimics significantly attenuated TBI-induced up-regulation of Puma, Noxa and Bax mRNA compared to TBI mice injected with negative control miR mimic (FIG. 11B). In addition, miR-23a-3p and -27a-3p mimics also significantly attenuated the TBI-induced increase in PUMA, Noxa, Bax and active Bax protein levels in TBI cortex at 24 hours post-injury as compared to negative control miR mimics (FIG. 11C).

Figure 12:
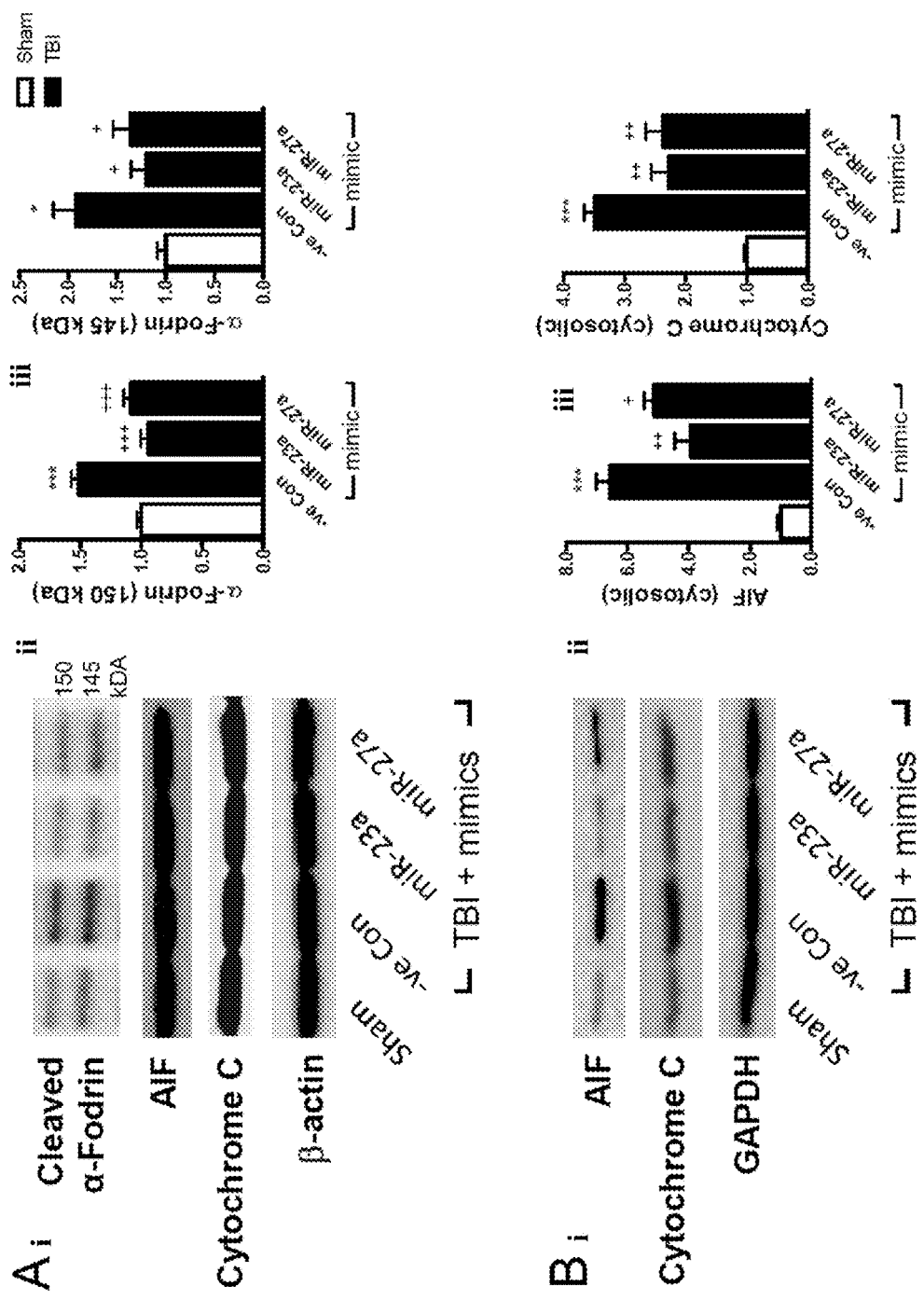
FIG. 12 shows that icy injection of miR-23a and miR-27a mimics attenuate neuronal apoptosis in injured cortex after TBI. (A) (i) Whole tissue lysates from mouse cortex 24 hours after TBI and icy injection of miR-23a-3p or -27a-3p or -ve Con mimics were fractioned on SDS-polyacrylamide gel and immunobloted with antibodies against α-Fodrin, AIF-1, cytochrome c and β-actin. Levels of cleaved α-Fodrin(ii) and (iii) in total lysates were quantified as fold change to the levels of sham after measurement of band intensity by densitometry. Data represent the mean± S.D. *-P<0.05; -P<0.01; *-P<0.001 vs. sham animals; +-P<0.05; ++-P<0.01;+++-P<0.001 vs. injured-ve Con miR mimics injected group (N=4-6). (B) (i) Cytosolic fractions from cortex tissues 24 hours after TBI and icy injection of miR-23a-3p or -27a-3p or -ve cnt mimics were fractioned on SDS-polyacrylamide gel and immunobloted with antibodies against AIF-1, cytochrome c and GAPDH. Levels of AIF-1 (ii) and cytochrome c (iii) proteins in cytosolic fraction of TBI miR mimics injected animals were quantified as fold change to the levels of sham after measurement of band intensity by densitometry. Data represent the mean± S.D. *-P<0.05; -P<0.01; *-P<0.001 vs. sham animals; +-P<0.05; ++-P<0.01;+++-P<0.001 vs. injured-ve cnt miR mimics injected group (N=4-6). Analysis by one-way ANOVA followed by multiple pairwise comparisons using Student-Newman-Keuls post-hoc test.
Figure 13:
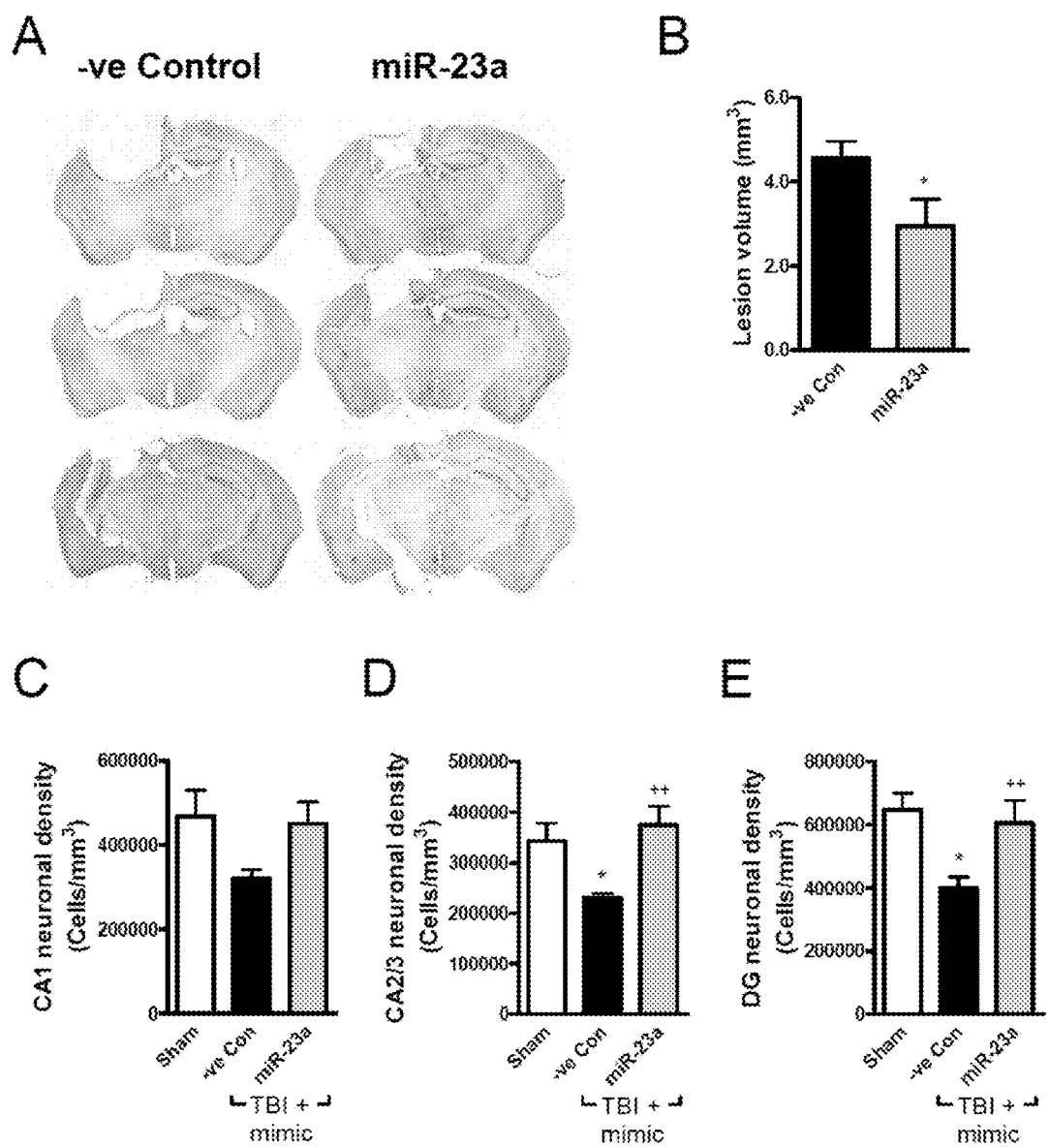
FIG. 13 shows that miR-23a treatment reduced lesion volume and neuronal loss in the cortex after TBI. Lesion volume was quantified using the Cavalieri method. Unbiased stereological assessment of lesion volume at 28 days after TBI was performed on cresyl violet-stained brain section. (A) Representative images from each group are shown. (B) Significant reduction of lesion volume was observed in miR-23a-3p mimic treated group (* p<0.05) when compared to the TBI negative miR mimic group. Analysis by student t-test, Mean±S.E.M, n=9. Stereological assessment of neuronal cell on PID28 was performed on cresyl-violet stained sections in the CA1 (C), CA2/3 (D), and DG (E) sub-regions of cortex. Significant differences of neuronal density were observed between sham-injured and TBI negative miR mimic groups in the CA2/3 (*p<0.05), DG (*p<0.05) sub-regions of cortex. miR-23a-3p mimic treatment significantly increased neuronal density in the CA2/3 (##p<0.01), DG (##p<0.01) cortex compared with TBI negative miR mimic group. Analysis by one-way ANOVA followed by Student's Newman-Keuls test , Mean±S.E.M, n=6-9.

The effect of icv injection with miR-23a-3p, -27a-3p and negative control miR mimics was also examined on multiple apoptosis markers in the TBI cortex at 24 hours post-injury. Quantitative Western blot analysis demonstrated that miR-23a-3p and -27a-3p did not change the levels of key pro-apoptotic proteins, such as AIF-1 and cytochrome c in whole tissue lysates as compared to negative control miR mimics. In addition, icv injection of miR-23a-3p and -27a-3p mimics significantly attenuated cleavage of a-Fodrin (FIG. 12A). Analysis of cytosolic extracts revealed that miR-23-3p and miR-27a-3p mimics significantly reduced TBI-induced release of AIF and cytochrome c into the cytosol (FIG. 12B).

miR-23a mimic treatment reduced lesion volume and neuronal loss in the hippocampus after TBI. TBI-induced lesion volume at 28 days post-injury was quantified in cresyl violet stained coronal brain sections by stereological methods in animals that received either negative control miR mimic or miR-23a-3p mimic (chosen based on the relative strength of anti-apoptotic effects). miR-23a-3p injection significantly reduced TBI induced lesion volumes compared to the negative control miR mimic group (FIG. 13A,B; -ve control=4.561 mm$^3$±0.4099 and miR-23a=2.941 mm$^3$±0.6468, n=9). TBI-induced neuronal loss in the CA1, CA2/3 and DG sub-regions of hippocampus at 28 days post injury was quantified in cresyl violet stained brain sections by stereological methods from sham-injured, TBI+negative control miR mimic, and TBI+miR-23a-3p mimic groups. No significant effect of miR-23a mimic treatment was observed in CA1 neuronal densities (FIG. 13C), although a neuroprotective trend was observed. Importantly, administration of miR-23a-3p significantly attenuated TBI-induced neuronal loss in CA2/3 (FIG. 13D) and DG (FIG. 13E) compared to the TBI negative control miR mimic group.

Discussion

The modulation of apoptotic mechanisms by select miRs has been described in cerebral ischemia models (Siegel et al., 2011; Selvamani et al., 2012). miR-29b inhibits apoptosis during neuronal maturation by targeting pro-apoptotic BH3-only genes (Kole et al., 2011), and miR-223 is neuroprotective by lowering levels of specific glutamate receptors (Harraz et al., 2012). Recent studies demonstrated that miR-34a, miR-451, and miR-874 increased vulnerability in transfected neurons in vitro (Truettner et al., 2013). In a rat TBI model, Redell et al. described changes impacting miR-21 and some of its known and predicted targets, but without demonstrating a causal relationship between miRNA changes and TBI-induced neuronal cell death (Redell et al., 2011). Shown herein is the first detailed characterization of specific miR changes in the injured cortex following TBI, and the elucidation of their effects on neuronal cell death mechanisms. A temporal profiling was performed of miR-NAs that were altered in the acute period after experimental TBI in mice, and selected miRs which were rapidly down-regulated in the first 24 h after TBI, a time period associated with intense activation of neuronal cell death pathways (Stoica and Faden, 2010). Out of 36 miRs down-regulated after TBI (data not shown) only three, miR-23a-3p, -27a-3p and -143 declined rapidly in the first hours after trauma and returned to normal levels several days later. It is theorized that this pattern reflects an active regulation and selective involvement in the acute secondary neuronal cell death mechanisms that characterize the early post-traumatic period (Di Giovanni et al., 2003). Both miR-23a and -27a were concentrated on because they are the members of the same genomic cluster.

Changes in miR-23a and miR-27a after TBI in rat have been reported, but no detailed analysis (qPCR) or exploration of mechanisms has heretofore been performed. Hu et al. showed that miR-23a* (miR-23a-5p), different from the miR-23a-3p under investigation here, was increased at 24 h after rat CCI in the injured hippocampus (Hu et al., 2012). Another study mentioned miR-23a-3p expression following rat lateral fluid percussion, but the data as presented were insufficient to determine if changes were significant (Lei et al., 2009). Truettner at al. observed that miR-27a and miR-27b were decreased in the injured cortex at 7 h after rat TBI following treatment with hypothermia, although the data with normothermia were inconclusive (Truettner et al., 2011). Another recent study reported that miR-27a increased in the hippocampus following status epilepticus, but the relationship to cell death was not examined (Jimenez-Mateos et al., 2011).

It is theorized herein that decreases of miR-23a-3p and -27a-3p results in the up-regulation of their pro-apoptotic targets. mRNA target prediction analysis (TargetScan, miRecords, PITA) identified multiple pro-apoptotic genes that are potential targets for miR-23a-3p and-27a-3p-including the p53 tumor suppressor protein, a key modulator of DNA damage-induced cell death. p53 activation is mediated via phosphorylation at Ser1S and Ser20 (Shieh et al., 1997), and it was observed herein rapid up-regulation and activation/phosphorylation of p53 at Ser1S after TBI. DNA damage, a key feature of etoposide-induced neuronal cell death results in increased levels of phosphorylated histone H2A.X (Ser139) (Rogakou et al., 1999) and induces p53 up-regulation and activation/phosphorylation. In turn, p53 induces various pro-apoptotic Bcl2 family molecules and apoptosis (Lowe et al., 1993).

Other predicted targets for miR-23a-3p and-27a-3p include pro-apoptotic members of Bcl-2 family such as BH3-only members PUMA and Noxa as well as multi BH domain Bcl2 family member BAX, (Oda et al., 2000; Nakano and Vousden, 2001; Kaeser and Iggo, 2002). As shown herein, after TBI, rapid increase of mRNA levels of PUMA and Noxa was observed. Their expression peaked between 1-24 h post-injury and later declined, consistent with regulation by miR-23a-3p and -27a-3p. Protein analysis confirmed that TBI induced rapid increases in the levels of Puma, Noxa and Bax. PUMA and Noxa induce direct as well as indirect activation of Bax resulting in its translocation to the mitochondria followed by mitochondrial outer membrane permeabilization and the release of mitochondrial apoptogenic proteins, including cytochrome c and AIF-1 (Liu et al., 1996; Susin et al., 1999);(Nakano and Vousden, 2001). Notably, cortical neurons are resistant to apoptosis in the absence of PUMA and Noxa (Steckley et al., 2007).

As shown herein, miR-23a and -27a down-regulation occurred rapidly after etoposide treatment and lasted for at least 24 h, and as in the in vivo TBI model it was paralleled by significant increases in PUMA, Noxa and Bax (total and activated). The expression of miR-23-3p and -27a-3p in neuroglia was much smaller compared to primary neurons (data not shown), suggesting that the changes observed in vivo likely reflect neuronal events.

Etoposide induces caspase-dependent and caspase-independent neuronal apoptosis via release from mitochondria into the cytosol of cytochrome c and AIF, respectively (Culmsee and Mattson, 2005). The pro-apoptotic effect of these molecules in neuronal apoptosis involves changes in sub-cellular localization without modifying expression levels (Sabirzhanov et al., 2012). Cytosolic cytochrome c leads to activation of caspases (Li et al., 1997; Srinivasula et al., 1998), cleavage of caspase substrates, such as PARP and cell death (Le Rhun et al., 1998). Cytosolic AIF-1 translocates to the nucleus mediating caspase-independent apoptosis (Susin et al., 1999). After both mouse CCI in vivo and etoposide treatment in primary cortical neurons in vitro, cytochrome c release and PARP cleavage as well as AIF release all were observed.

As shown herein, administration of miR-23a and -27a mimics resulted in attenuation of etoposide-induced neuronal cell death (p53-dependent apoptosis) and caspase activity. Conversely, treatment with miR-23a and -27a hairpin inhibitors that attenuate miR levels enhanced neuronal apoptosis. Together these data demonstrate the important role played by miR-23a and -27a decline in neuronal cell death. Neither miR-23a nor miR-27a mimics affected p53 expression or phosphorylation, or caused changes in histone H2A.X phosphorylation. It is conclude herein that miR-23a and -27a modulate neither the etoposide-induced DNA damage nor the subsequent activation of p53. Rather, it is proposed that miR-23a and -27a target pro-apoptotic genes downstream of p53 such as PUMA, Noxa and Bax. The luciferase assays confirmed that miR-23a-3p and -27a-3p target PUMA, Noxa and Bax 3'UTR mRNA. Consistent with this conclusion, transfection of neurons with miR-23a-3p or miR-27a-3p mimics caused significant down-regulation of PUMA, Noxa and Bax in vitro. Transfection with miR-23a-3p or miR-27a-3p mimics decreased the levels of AIF-1 and cytochrome c in the cytosolic fraction of etoposide-treated primary cortical neurons and reduced cleavage of caspase-3 and PARP. a-Fodrin undergoes both calpain-dependent cleavage (150/145 kDa fragments) and caspase-dependent cleavage (150/120 kDa fragments) after brain injury in vivo (Siman et al., 2004) and apoptosis in vitro (Cryns et al., 1996). Transfection of primary cortical neurons with miRs-23a and -27a mimics inhibited cleavage of a-Fodrin, and reduced both calpain-dependent and caspase-dependent fragments.

The importance of miR-23a and -27a changes for TBI-induced activation of neuronal cell death pathways was demonstrated by icy injection of miR-23a-3p and -27a-3p mimics. These interventions not only attenuated injury-dependent activation of PUMA, Noxa and Bax, but also inhibited downstream molecular mechanisms of neuronal apoptosis in the TBI cortex. Thus, treatment with miR-23a-3p and miR-27a-3p mimics down regulates release of AIF-1 and cytochrome c into the cytosol after TBI, and inhibits both calpain-dependent and caspase-dependent a-Fodrin cleavage. Moreover, the data shown herein demonstrate that interventions targeting selected miRs has the ability to attenuate tissue loss and hippocampal neurodegeneration after TBI. Specifically, icy administration of miR-23a-3p mimic (selected based on the strength of its molecular effects) reduced cortical lesion volume as well as neuronal cell loss in key regions of the hippocampus, such as CA2/3 and DG, which are well-established sites of post-traumatic secondary injury (Kabadi et al., 2012).

A recent study proposes that miR-23/27 regulate the sensitivity of neurons to apoptosis in fetal hypoxia through negative modulation of Apaf-1 expression (Chen et al., 2014). Although no changes were observed herein in Apaf-1 during neuronal apoptosis in vitro (FIG. 7) (Sabirzhanov et al., 2012) up-regulation of Apaf-1 following adult TBI has been reported (Yakovlev et al., 2001). Thus, it is possible that in addition to regulating upstream cell death molecules such as pro-apoptotic Bcl2 proteins, miR-23/27 also modulate apoptosis through regulation of downstream targets such as Apaf-1.

In summary, the results shown herein demonstrated that miR-23a and -27a target pro-apoptotic members of Bcl-2 family Bax, PUMA and Noxa. Down-regulation of miR-23a-3p and-27a-3p after TBI or neuronal apoptosis in vitro amplifies p53-dependent apoptotic pathways and contributes to neuronal cell death in vivo and in vitro. Treatment with mimics of these miRs attenuates neuronal apoptosis and significantly reduced post-traumatic neurodegeneration. The distinct ability of miRs to target multiple members of a molecular pathway, as shown herein, may explain the significance of their biological effects. Thus, miR-23a and -27a mimics can act as therapeutic agents for modulation of neuronal apoptosis after TBI.

REFERENCES

The contents of all references cited herein are incorporated by reference herein for all purposes.

Babar I. A.; Cheng, C. J.; Booth, C. J.; Liang, X.; Weidhaas, J. B.; Saltzman, W. M.; Slack, F. J. Nanoparticle-based therapy in an in vivo microRNA-155 (miR-155)-dependent mouse model of lymphoma. Proc. Natl. Acad. Sci. USA 2012, 109, E1695-E1704.

Chen Q, Xu J, Li L, Li H, Mao S, Zhang F, Zen K, Zhang C Y, Zhang Q (2014) MicroRNA-23a/b and microRNA-27a/b suppress Apaf-1 protein and alleviate hypoxia-induced neuronal apoptosis. Cell death & disease 5:e1132.

Clark R S B, Chen M, Kochanek P M, Watkins S C, Jin K L, Draviam R, Nathaniel P D, Pinto R, Marion D W, Graham S H (2001) Detection of single- and double-strand DNA breaks after traumatic brain injury in rats: comparison of in situ labeling techniques using DNA polymerase I, the Klenow fragment of DNA polymerase I, and terminal deoxynucleotidyl transferase. Journal of Neurotrauma 18:675-689.

Cryns V L, Bergeron L, Zhu H, Li H, Yuan J (1996) Specific cleavage of alpha-fodrin during Fas- and tumor necrosis factor-induced apoptosis is mediated by an interleukin-1beta-converting enzyme/Ced-3 protease distinct from the poly(ADP-ribose) polymerase protease. J Biol Chem 271:31277-31282.

Culmsee C, Mattson M P (2005) p53 in neuronal apoptosis. Biochem Biophys Res Commun 331:761-777.

Di Giovanni S, Knoblach S M, Brandoli C, Aden S A, Hoffman E P, Faden A I (2003) Gene profiling in spinal cord injury shows role of cell cycle in neuronal death. Annals of Neurology 53:454-468.

Engel T, Plesnila N, Prehn J H, Henshall D C (2011) In vivo contributions of BH3-only proteins to neuronal death following seizures, ischemia, and traumatic brain injury. J Cereb Blood Flow Metab 31:1196-1210.

Fox G B, Fan L, Levasseur R A, Faden A I (1998) Sustained sensory/motor and cognitive deficits with neuronal apoptosis following controlled cortical impact brain injury in the mouse. Journal of Neurotrauma 15:599-614.

Gautier L, Cope L, Bolstad B M, Irizarry R A (2004) affy—analysis of Affymetrix GeneChip data at the probe level. Bioinformatics 20:307-315.

Gentleman R (2005) Bioinformatics and computational biology solutions using R and Bioconductor. New York: Springer Science+Business Media.

Griffiths-Jones S, Grocock RJ, van Dongen S, Bateman A, Enright AJ (2006) miRBase: microRNA sequences, targets and gene nomenclature. Nucleic Acids Res 34:D140-144.

Guo Z, Zhou B, Liu W, Xu Y, Wu D, Yin Z, Permatasari F, Luo D (2013) MiR-23a regulates DNA damage repair and apoptosis in UVB-irradiated HaCaT cells. J Dermatol Sci 69:68-76.

Harraz M M, Eacker S M, Wang X, Dawson T M, Dawson V L (2012) MicroRNA-223 is neuroprotective by targeting glutamate receptors. Proc Natl Acad Sci USA 109:18962-18967.

Hwang, D. W.; Son, S.; Jang, J.; Youn, H.; Lee, S.; Lee, D.; Lee, Y.-S.; Jeong, J. M.; Kim, W. J.;

Lee, D. S. A brain-targeted rabies virus glycoprotein-disulfide linked PEI nanocarrier for delivery of neurogenic microRNA. Biomaterials 2011, 32, 4968-4975.

Hu Z, Yu D, Almeida-Suhett C, Tu K, Marini A M, Eiden L, Braga MF, Zhu J, Li Z (2012) Expression of miRNAs and their cooperative regulation of the pathophysiology in traumatic brain injury. PLoS One 7:e39357.

Irizarry R A, Bolstad B M, Collin F, Cope L M, Hobbs B, Speed T P (2003) Summaries of Affymetrix GeneChip probe level data. Nucleic Acids Res 31:e15.

Jeffers J R, Parganas E, Lee Y, Yang C, Wang J, Brennan J, MacLean K H, Han J, Chittenden T, Ihle J N, McKinnon P J, Cleveland J L, Zambetti G P (2003) Puma is an essential mediator of p53-dependent and -independent apoptotic pathways. Cancer cell 4:321-328.

Jimenez-Mateos E M, Henshall D C (2013) Epilepsy and microRNA. Neuroscience 238:218-229.

Jimenez-Mateos E M, Bray I, Sanz-Rodriguez A, Engel T, McKiernan R C, Mouri G, Tanaka K, Sano T, Saugstad J A, Simon R P, Stallings R L, Henshall D C (2011) miRNA Expression profile after status epilepticus and hippocampal neuroprotection by targeting miR-132. The American journal of pathology 179:2519-2532.

Kabadi S V, Stoica B A, Hanscom M, Loane D J, Kharebava G, Murray Ii M G, Cabatbat R M, Faden A I (2012) CR8, a selective and potent CDK inhibitor, provides neuroprotection in experimental traumatic brain injury. Neurotherapeutics: The journal of the American Society for Experimental NeuroTherapeutics 9:405-421.

Kaeser M D, Iggo R D (2002) Chromatin immunoprecipitation analysis fails to support the latency model for regulation of p53 DNA binding activity in vivo. Proc Natl Acad Sci USA 99:95-100.

Kole A J, Swahari V, Hammond S M, Deshmukh M (2011) miR-29b is activated during neuronal maturation and targets BH3-only genes to restrict apoptosis. Genes Dev 25:125-130.

Le Rhun Y, Kirkland J B, Shah G M (1998) Cellular responses to DNA damage in the absence of Poly(ADP-ribose) polymerase. Biochem Biophys Res Commun 245:1-10.

Lei P, Li Y, Chen X, Yang S, Zhang J (2009) Microarray based analysis of microRNA expression in rat cerebral cortex after traumatic brain injury. Brain Res 1284:191-201.

Li P, Nijhawan D, Budihardjo I, Srinivasula S M, Ahmad M, Alnemri E S, Wang X (1997) Cytochrome c and dATP-dependent formation of Apaf-1/caspase-9 complex initiates an apoptotic protease cascade. Cell 91:479-489.

Liu D Z, Tian Y, Ander B P, Xu H, Stamova B S, Zhan X, Turner R J, Jickling G, Sharp F R (2010) Brain and blood microRNA expression profiling of ischemic stroke, intracerebral hemorrhage, and kainate seizures. J Cereb Blood Flow Metab 30:92-101.

Liu X, Kim C N, Yang J, Jemmerson R, Wang X (1996) Induction of apoptotic program in cell-free extracts: requirement for dATP and cytochrome c. Cell 86:147-157.

Livak K J, Schmittgen T D (2001) Analysis of relative gene expression data using real-time quantitative PCR and the 2(-Delta Delta C(T)) Method. Methods 25:402-408.

Loane D J, Pocivaysek A, Moussa C E, Thompson R, Matsuoka Y, Faden A I, Rebeck G W, Burns M P (2009) Amyloid precursor protein secretases as therapeutic targets for traumatic brain injury. Nature medicine 15:377-379.

Lomonosova E, Chinnadurai G (2008) BH3-only proteins in apoptosis and beyond: an overview. Oncogene 27 Suppl 1:S2-19.

Lowe S W, Schmitt E M, Smith S W, Osborne B A, Jacks T (1993) p53 is required for radiation-induced apoptosis in mouse thymocytes. Nature 362:847-849.

Nakano K, Vousden K H (2001) PUMA, a novel proapoptotic gene, is induced by p53. Mol Cell 7:683-694.

Oda E, Ohki R, Murasawa H, Nemoto J, Shibue T, Yamashita T, Tokino T, Taniguchi T, Tanaka N (2000) Noxa, a BH3-only member of the Bcl-2 family and candidate mediator of p53-induced apoptosis. *Science* 288:1053-1058.

Pfaffl M W (2001) A new mathematical model for relative quantification in real-time RT-PCR. *Nucleic Acids Res* 29:e45.

Pietrzak M, Smith S C, Geralds J T, Hagg T, Gomes C, Hetman M (2011) Nucleolar disruption and apoptosis are distinct neuronal responses to etoposide-induced DNA damage. *Journal of Neurochemistry* 117:1033-1046.

Redell J B, Liu Y, Dash P K (2009) Traumatic brain injury alters expression of hippocampal microRNAs: potential regulators of multiple pathophysiological processes. *J Neurosci Res* 87:1435-1448.

Redell J B, Zhao J, Dash P K (2011) Altered expression of miRNA-21 and its targets in the hippocampus after traumatic brain injury. *J Neurosci Res* 89:212-221.

Ren, Y.; Kang, C. S.; Yuan, X. B.; Zhou, X.; Xu, P.; Han, L.; Wang, G. X.; Jia, Z.; Zhong, Y.; Yu, S.; et al. Co-delivery of as-miR-21 and 5-FU by poly(amidoamine) dendrimer attenuates human
glioma cell growth in vitro. *J. Biomater. Sci.* 2010, 21, 303-314.

Rogakou E P, Boon C, Redon C, Bonner W M (1999) Megabase chromatin domains involved in DNA double-strand breaks in vivo. *J Cell Biol* 146:905-916.

Sabirzhanov B, Stoica B A, Hanscom M, Piao C S, Faden A I (2012) Over-expression of HSP70 attenuates caspase-dependent and caspase-independent pathways and inhibits neuronal apoptosis. *Journal of Neurochemistry* 123:542-554.

Selvamani A, Sathyan P, Miranda R C, Sohrabji F (2012) An antagomir to microRNA Let7f promotes neuroprotection in an ischemic stroke model. *PLoS One* 7:e32662.

Shamas-Din A, Brahmbhatt H, Leber B, Andrews D W (2011) BH3-only proteins: Orchestrators of apoptosis. *Biochimica et biophysica acta* 1813:508-520.

Shieh S Y, Ikeda M, Taya Y, Prives C (1997) DNA damage-induced phosphorylation of p53 alleviates inhibition by MDM2. *Cell* 91:325-334.

Siegel C, Li J, Liu F, Benashski S E, McCullough L D (2011) miR-23a regulation of X-linked inhibitor of apoptosis (XIAP) contributes to sex differences in the response to cerebral ischemia. *Proc Natl Acad Sci USA* 108:11662-11667.

Siman R, Baudry M, Lynch G (1984) Brain fodrin: substrate for calpain I, an endogenous calcium-activated protease. *Proc Natl Acad Sci USA* 81:3572-3576.

Siman R, McIntosh T K, Soltesz K M, Chen Z, Neumar R W, Roberts V L (2004) Proteins released from degenerating neurons are surrogate markers for acute brain damage. *Neurobiol Dis* 16:311-320.

Srinivasula S M, Ahmad M, Fernandes-Alnemri T, Alnemri E S (1998) Autoactivation of procaspase-9 by Apaf-1-mediated oligomerization. *Mol Cell* 1:949-957.

Stappert L, Borghese L, Roese-Koerner B, Weinhold S, Koch P, Terstegge S, Uhrberg M, Wernet P, Brustle O (2013) MicroRNA-based promotion of human neuronal differentiation and subtype specification. *PLoS One* 8:e59011.

Steckley D, Karajgikar M, Dale L B, Fuerth B, Swan P, Drummond-Main C, Poulter MO, Ferguson S S, Strasser A, Cregan SP (2007) Puma is a dominant regulator of oxidative stress induced Bax activation and neuronal apoptosis. *J Neurosci* 27:12989-12999.

Stoica B A, Faden A I (2010) Cell death mechanisms and modulation in traumatic brain injury. Neurotherapeutics: *The journal of the American Society for Experimental NeuroTherapeutics* 7:3-12.

Stoica B A, Movsesyan V A, Lea PMt, Faden A I (2003) Ceramide-induced neuronal apoptosis is associated with dephosphorylation of Akt, BAD, FKHR, GSK-3beta, and induction of the mitochondrial-dependent intrinsic caspase pathway. *Mol Cell Neurosci* 22:365-382.

Stoica B A, Movsesyan V A, Knoblach S M, Faden A I (2005) Ceramide induces neuronal apoptosis through mitogen-activated protein kinases and causes release of multiple mitochondrial proteins. *Mol Cell Neurosci* 29:355-371.

Susin S A, Lorenzo H K, Zamzami N, Marzo I, Snow B E, Brothers G M, Mangion J, Jacotot E, Costantini P, Loeffler M, Larochette N, Goodlett D R, Aebersold R, Siderovski D P, Penninger J M, Kroemer G (1999) Molecular characterization of mitochondrial apoptosis-inducing factor. *Nature* 397:441-446.

Truettner J S, Motti D, Dietrich W D (2013) MicroRNA overexpression increases cortical neuronal vulnerability to injury. *Brain Res* 1533:122-130.

Truettner J S, Alonso O F, Bramlett H M, Dietrich W D (2011) Therapeutic hypothermia alters microRNA responses to traumatic brain injury in rats. *J Cereb Blood Flow Metab* 31:1897-1907.

Vousden K H (2005) Apoptosis. p53 and PUMA: a deadly duo. *Science* 309:1685-1686.

Yakovlev A G, Di Giovanni S, Wang G, Liu W, Stoica B, Faden A I (2004) BOK and NOXA are essential mediators of p53-dependent apoptosis. *J Biol Chem* 279:28367-28374.

Yakovlev A G, Ota K, Wang G, Movsesyan V, Bao W L, Yoshihara K, Faden A I (2001) Differential expression of apoptotic protease-activating factor-1 and caspase-3 genes and susceptibility to apoptosis during brain development and after traumatic brain injury. *J Neurosci* 21:7439-7446.

Yan H, Xu T, Zhao H, Lee K C, Wang H Y, Zhang Y (2013) Isoflurane increases neuronal cell death vulnerability by downregulating miR-214. *PLoS One* 8:e55276.

Yang X, Zhou Y, Peng S, Wu L, Lin H Y, Wang S, Wang H (2012) Differentially expressed plasma microRNAs in premature ovarian failure patients and the potential regulatory function of mir-23a in granulosa cell apoptosis. *Reproduction* 144:235-244.

Ziu M, Fletcher L, Rana S, Jimenez D F, Digicaylioglu M (2011) Temporal differences in microRNA expression patterns in astrocytes and neurons after ischemic injury. *PLoS One* 6:e14724.

That which is claimed is:

1. A method for treating a brain injury due to a traumatic event in a mammalian subject in need of treatment thereof, the method comprising administering by intracerebroventricular injection to the mammal subject an effective amount of a miR-23a-3p and/or miR-27a-3p mimic to reduce activation of Puma, Noxa and Bax to reduce neuronal apoptosis, wherein the miR-23a-3p and/or miR-27a-3p mimic is administered within one hour to ten hours of the brain injury.

2. The method of claim 1, wherein the miR-23a-3p and miR-27a-3p mimic is a double stranded nucleic acid molecule.

3. The method of claim 1, wherein the miR-23a-3p and miR-27a-3p mimic comprises a nucleotide sequence of AUCACAUUGCCAGGGAUUUCC (SEQ ID NO: 1) and UUCACAGUGGCUAAGUUCCGC (SEQ ID NO: 2), respectively.

4. The method of claim 1, wherein the traumatic event is an inertia injury due to sudden acceleration or deceleration, an impact injury or a penetrating injury.

5. The method of claim 1, wherein the effective amount of the miR-23a-3p and/or miR-27a-3p mimic is from about 1 nanomole to about 1 micromole per kg of body weight.

6. The method of claim 5, wherein the effective amount of the miR-23a-3p and/or miR-27a-3p mimic is from about 10 nanomoles to about 100 nanomoles per kg of body weight.

7. A method of protecting neuronal cells from cell death, the method comprising the step of supplying to the neuronal cells an effective amount of at least one miRNA mimic selected from the group consisting of miR-23a-3p mimic and miR-27a-3p mimic in an amount sufficient to reduce levels of Puma, Noxa and Bax.

8. The method of claim 7, wherein the miR-23a-3p and miR-27a-3p mimics comprise a nucleotide sequence of AUCACAUUGCCAGGGAUUUCC (SEQ ID NO: 1) and UUCACAGUGGCUAAGUUCCGC (SEQ ID NO: 2), respectively.

9. A method for blocking a step in the apoptotic biochemical cascade to reduce neuronal tissue or cell death, the method comprising:

contacting neuronal tissue or cells with a miRNA mimic in an amount sufficient to target a pro-apoptotic gene downstream of p53 including PUMA, Noxa, and/or Bax and cause down-regulation of PUMA, Noxa, and/or Bax, wherein the miRNA mimic is selected from the group consisting of miR-23a-3p and miR-27a-3p mimics.

10. The method of claim 9, wherein the neuronal tissues or cells are transfected with the miRNA mimic.

11. The method of claim 9, wherein the miR-23a-3p and miR-27a-3p mimics comprise a nucleotide sequence of AUCACAUUGCCAGGGAUUUCC (SEQ ID NO: 1) and UUCACAGUGGCUAAGUUCCGC (SEQ ID NO: 2), respectively.

* * * * *